US012699807B2

(12) United States Patent
Jannink et al.

(10) Patent No.: US 12,699,807 B2
(45) Date of Patent: Aug. 4, 2026

(54) SYSTEMS AND METHODS FOR ANONYMIZING PRIVATE DATA FOR USE IN MACHINE LEARNING MODELS

(71) Applicant: Synthpop Inc., Wellesley, MA (US)

(72) Inventors: Jan Jannink, Menlo Park, CA (US); Elad Ferber, Wellesley, MA (US)

(73) Assignee: Synthpop Inc., Wellesley, MA (US)

( * ) Notice: Subject to any disclaimer, the term of this patent is extended or adjusted under 35 U.S.C. 154(b) by 77 days.

(21) Appl. No.: 18/646,090

(22) Filed: Apr. 25, 2024

(65) Prior Publication Data

US 2024/0362363 A1 Oct. 31, 2024

Related U.S. Application Data

(60) Provisional application No. 63/509,516, filed on Jun. 21, 2023, provisional application No. 63/499,197, filed on Apr. 28, 2023.

(51) Int. Cl.
| | |
|---|---|
| *G06F 21/62* | (2013.01) |
| *G06F 40/205* | (2020.01) |
| *G06F 40/284* | (2020.01) |
| *G06V 30/10* | (2022.01) |
| *G16H 10/60* | (2018.01) |

(52) U.S. Cl.
CPC ........ *G06F 21/6254* (2013.01); *G06F 40/205* (2020.01); *G06F 40/284* (2020.01); *G06V 30/10* (2022.01); *G16H 10/60* (2018.01)

(58) Field of Classification Search
CPC .. G06F 21/6254; G06F 40/205; G06F 40/284; G06V 30/10; G16H 10/60
USPC ........................................................ 726/26
See application file for complete search history.

(56) References Cited

U.S. PATENT DOCUMENTS

| | | | | |
|---|---|---|---|---|
| 7,383,183 B1 * | 6/2008 | Davis | ..................... | G16H 10/60 |
| | | | | 704/235 |
| 11,507,540 B1 * | 11/2022 | Todd | ...................... | G06N 20/00 |
| 12,223,259 B1 * | 2/2025 | Sembium Varadarajan | ................ | |
| | | | | G06F 21/6254 |
| 2007/0081428 A1 * | 4/2007 | Malhotra | ............... | G16H 15/00 |
| | | | | 369/25.01 |
| 2013/0124523 A1 * | 5/2013 | Rogers | ................... | G16H 10/60 |
| | | | | 707/741 |
| 2021/0256160 A1 * | 8/2021 | Hachey | .................. | G06N 20/20 |

(Continued)

OTHER PUBLICATIONS

Moor et al. (Apr. 2023). "Foundation models for generalist medical artificial intelligence," Nature 616; pp. 259-265.

*Primary Examiner* — David P Zarka
(74) *Attorney, Agent, or Firm* — Morrison & Foerster LLP

(57) ABSTRACT

Described herein are techniques for performing a task using a trained external machine learning model. In some embodiments, a user request comprising a task and one or more protected health information (PHI) parameters associated with a patient may be received. Using one or more trained machine learning models, the PHI parameters may be extracted and a revised user request may be generated by replacing the PHI parameters with one or more synthetic PHI parameters. The revised user request may be provided to the trained external machine learning model and a response to the task comprising the synthetic PHI parameters may be received. The trained machine learning models may generate a revised response to the task by replacing the synthetic PHI parameters with the PHI parameters of the user request.

17 Claims, 22 Drawing Sheets

(56) References Cited

U.S. PATENT DOCUMENTS

| 2022/0068443 | A1* | 3/2022 | Ransom | G16H 10/20 |
|---|---|---|---|---|
| 2023/0031757 | A1* | 2/2023 | Bronson | G16H 15/00 |
| 2023/0046367 | A1* | 2/2023 | Doyen | G06V 30/153 |
| 2023/0282322 | A1* | 9/2023 | Rajkumar | G16H 10/60 |
| | | | | 705/3 |
| 2023/0395063 | A1* | 12/2023 | Ganong, III | G10L 15/26 |
| 2024/0095455 | A1* | 3/2024 | Sharma | G16H 10/60 |
| 2024/0242805 | A1* | 7/2024 | Dittmer | G16H 50/30 |
| 2024/0257967 | A1* | 8/2024 | Sandler | G16H 15/00 |
| 2025/0336543 | A1* | 10/2025 | Anthapur | G16H 10/60 |

* cited by examiner

User Request <u>204</u>

<u>Celia Johnson</u>, <u>MRN 12033313</u>, from <u>Cambridge, MA</u> is a <u>26-month-old</u> toddler had a <u>plantar fascia injury</u> in her <u>left leg</u> and we need to decide on whether to operate or not. Write a letter to her insurer, <u>Insurance A</u>, that would justify a thorough examination by a pediatric orthopedist.

FIG. 3

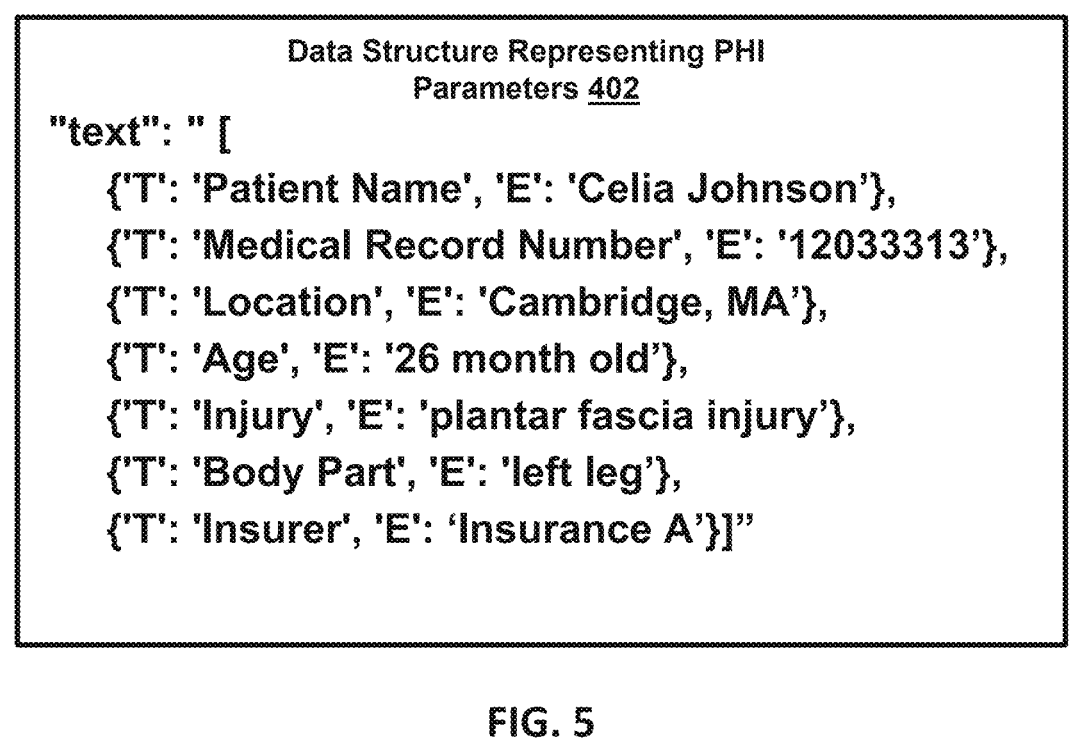

Data Structure Representing PHI
Parameters 402

"text": " [

{'T': 'Patient Name', 'E': 'Celia Johnson'},

{'T': 'Medical Record Number', 'E': '12033313'},

{'T': 'Location', 'E': 'Cambridge, MA'},

{'T': 'Age', 'E': '26 month old'},

{'T': 'Injury', 'E': 'plantar fascia injury'},

{'T': 'Body Part', 'E': 'left leg'},

{'T': 'Insurer', 'E': 'Insurance A'}]"

FIG. 5

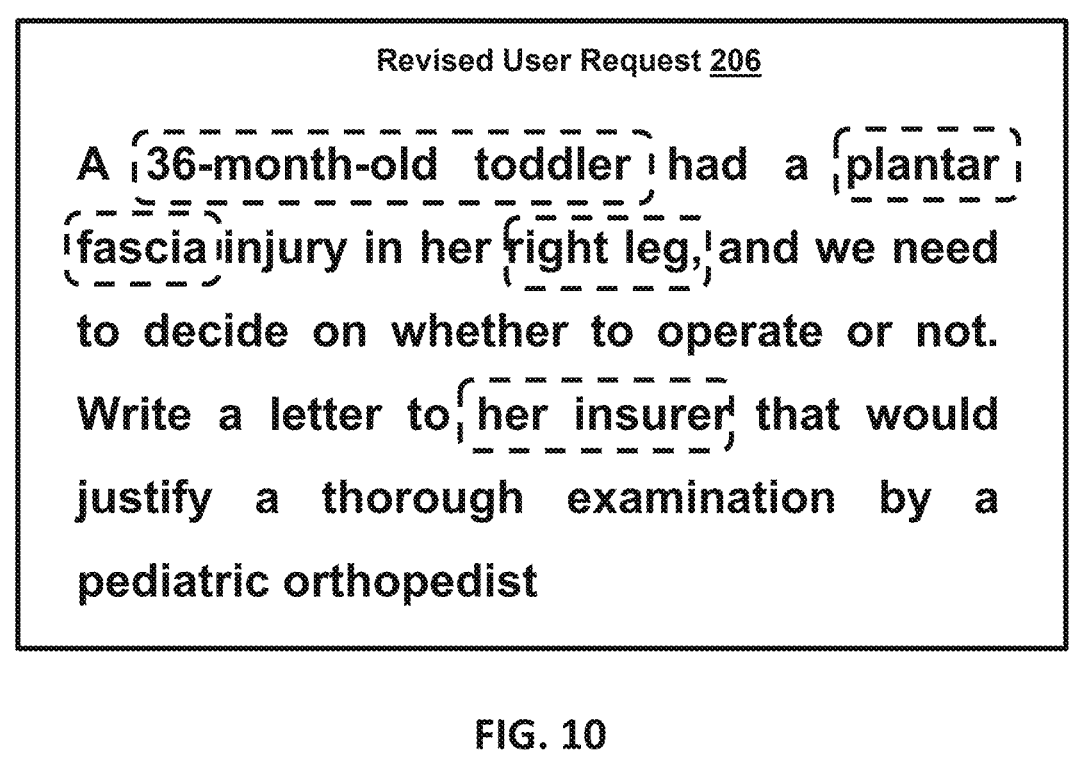

Revised User Request 206

A 36-month-old toddler had a plantar fascia injury in her right leg, and we need to decide on whether to operate or not. Write a letter to her insurer that would justify a thorough examination by a pediatric orthopedist

FIG. 10

| PHI Parameter | Value | Clinical Relevance | Modification Criteria |
|---|---|---|---|
| injury | plantar fascia injury | 0.95 | equal |
| age | 26-month-old | 0.91 | 18-36 months of age |
| body part | Left leg | 0.89 | Left or right leg but not both |
| location | Cambridge, MA | 0.1 | US based |
| Medical Record Number | 12033313 | 0.001 | Not required |
| Patient Name | Celia Johnson | 0.001 | Not required |
| Insurer | Insurance Healthcare A | 0.001 | Not required |

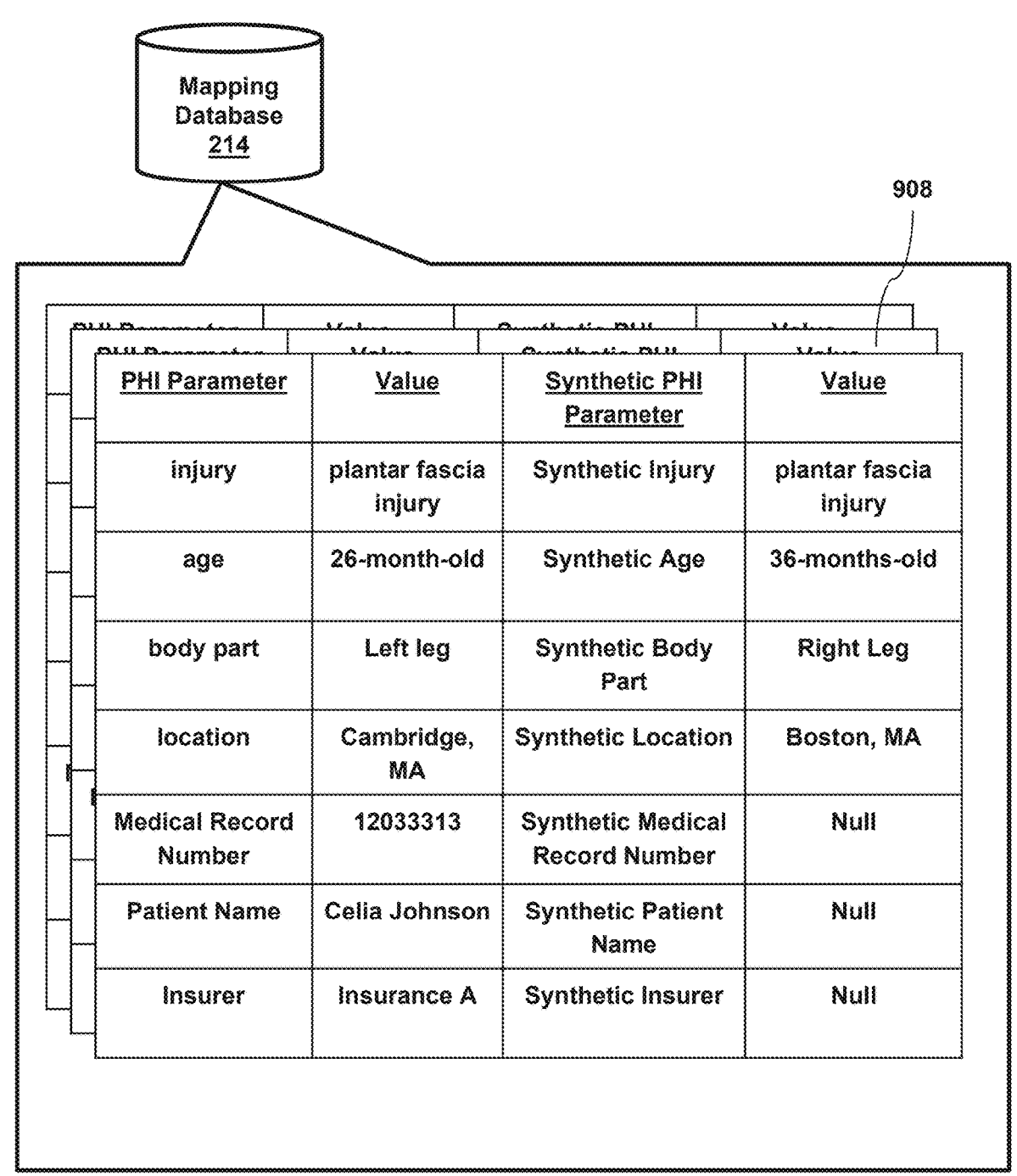

| PHI Parameter | Value | Synthetic PHI Parameter | Value |
|---|---|---|---|
| injury | plantar fascia injury | Synthetic Injury | plantar fascia injury |
| age | 26-month-old | Synthetic Age | 36-months-old |
| body part | Left leg | Synthetic Body Part | Right Leg |
| location | Cambridge, MA | Synthetic Location | Boston, MA |
| Medical Record Number | 12033313 | Synthetic Medical Record Number | Null |
| Patient Name | Celia Johnson | Synthetic Patient Name | Null |
| Insurer | Insurance A | Synthetic Insurer | Null |

Mapping Database 214

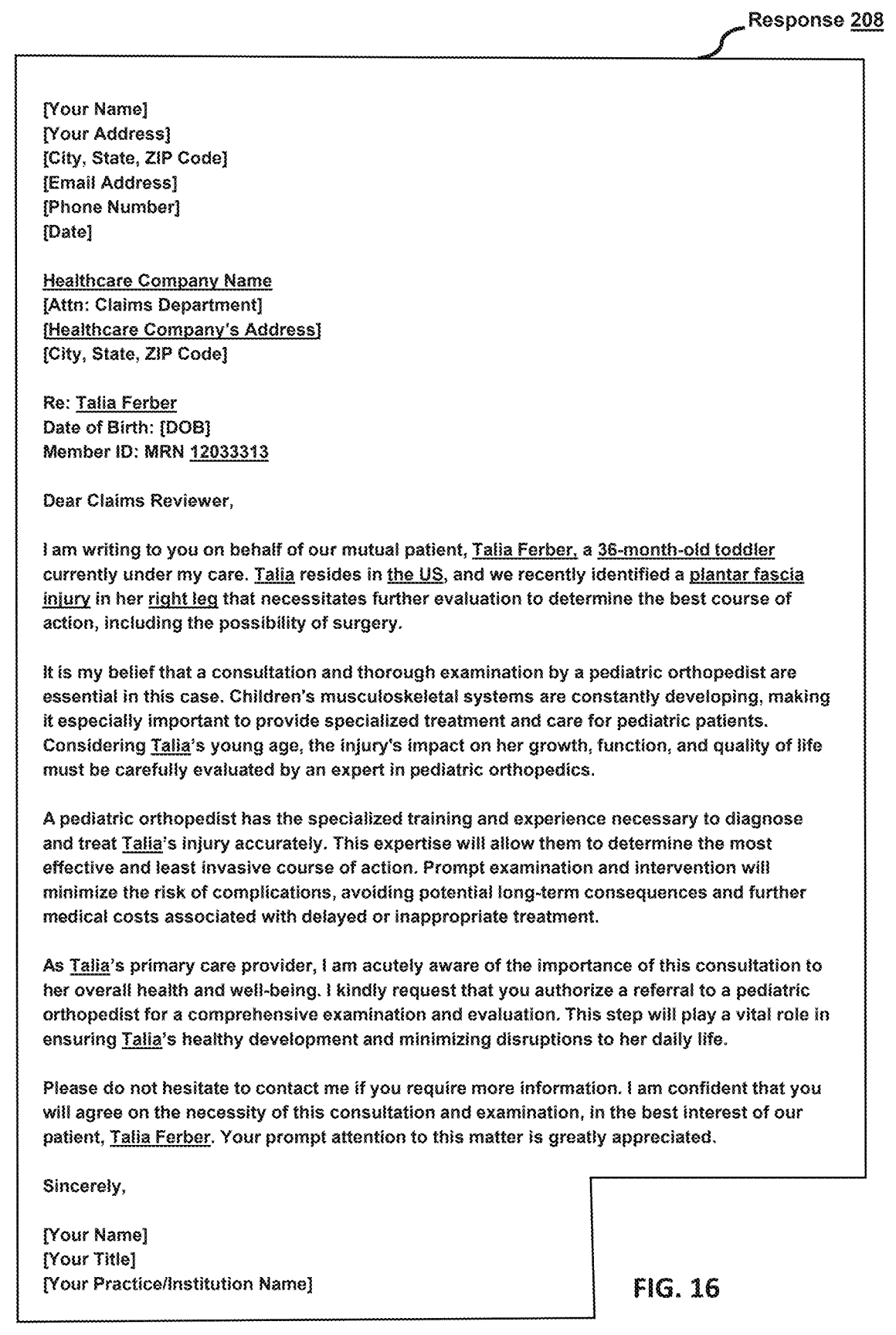

Response 208

[Your Name]
[Your Address]
[City, State, ZIP Code]
[Email Address]
[Phone Number]
[Date]

Healthcare Company Name
[Attn: Claims Department]
[Healthcare Company's Address]
[City, State, ZIP Code]

Re: Talia Ferber
Date of Birth: [DOB]
Member ID: MRN 12033313

Dear Claims Reviewer,

I am writing to you on behalf of our mutual patient, Talia Ferber, a 36-month-old toddler currently under my care. Talia resides in the US, and we recently identified a plantar fascia injury in her right leg that necessitates further evaluation to determine the best course of action, including the possibility of surgery.

It is my belief that a consultation and thorough examination by a pediatric orthopedist are essential in this case. Children's musculoskeletal systems are constantly developing, making it especially important to provide specialized treatment and care for pediatric patients. Considering Talia's young age, the injury's impact on her growth, function, and quality of life must be carefully evaluated by an expert in pediatric orthopedics.

A pediatric orthopedist has the specialized training and experience necessary to diagnose and treat Talia's injury accurately. This expertise will allow them to determine the most effective and least invasive course of action. Prompt examination and intervention will minimize the risk of complications, avoiding potential long-term consequences and further medical costs associated with delayed or inappropriate treatment.

As Talia's primary care provider, I am acutely aware of the importance of this consultation to her overall health and well-being. I kindly request that you authorize a referral to a pediatric orthopedist for a comprehensive examination and evaluation. This step will play a vital role in ensuring Talia's healthy development and minimizing disruptions to her daily life.

Please do not hesitate to contact me if you require more information. I am confident that you will agree on the necessity of this consultation and examination, in the best interest of our patient, Talia Ferber. Your prompt attention to this matter is greatly appreciated.

Sincerely,

[Your Name]
[Your Title]
[Your Practice/Institution Name]

FIG. 16

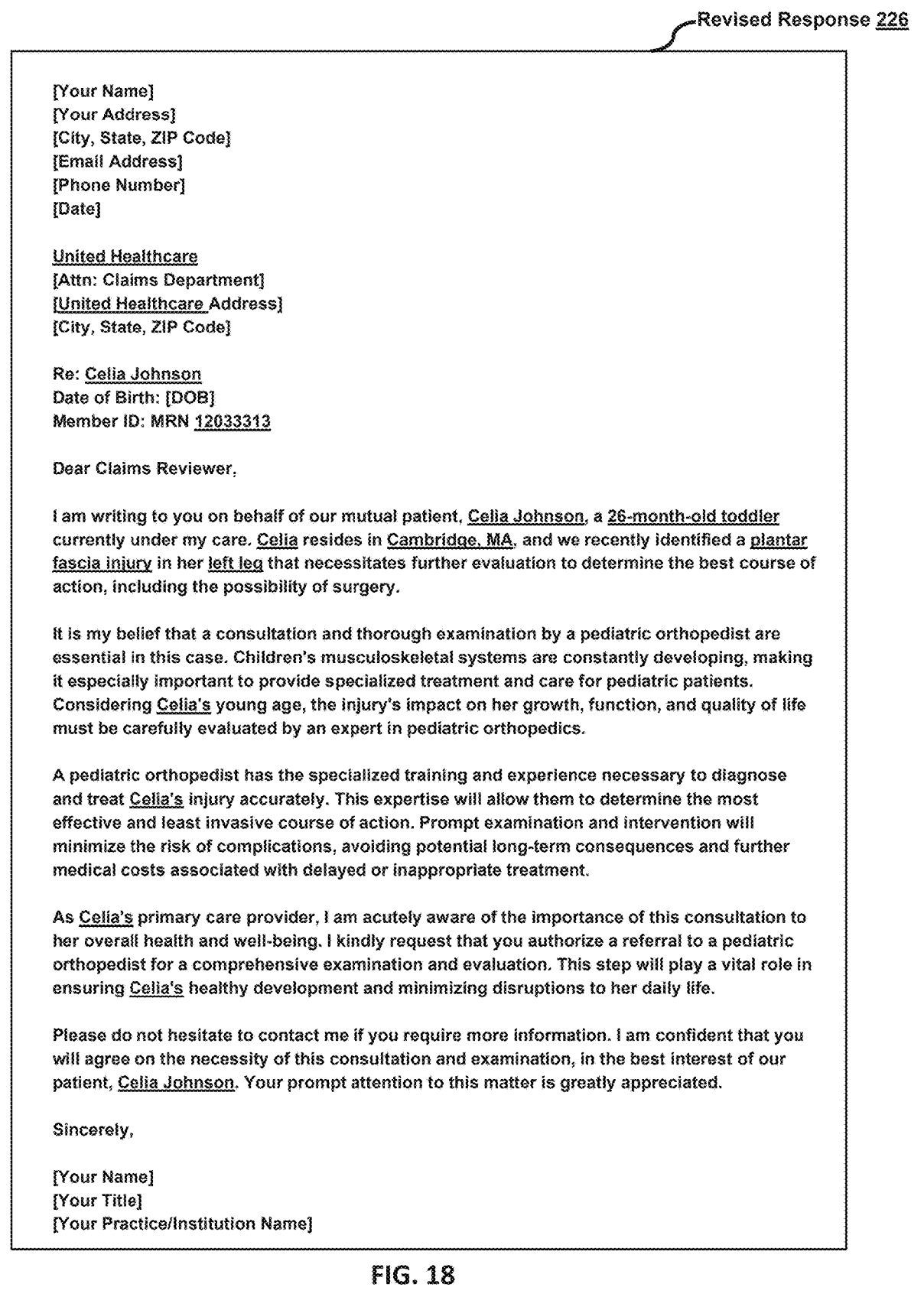

Revised Response 226

[Your Name]
[Your Address]
[City, State, ZIP Code]
[Email Address]
[Phone Number]
[Date]

United Healthcare
[Attn: Claims Department]
[United Healthcare Address]
[City, State, ZIP Code]

Re: Celia Johnson
Date of Birth: [DOB]
Member ID: MRN 12033313

Dear Claims Reviewer,

I am writing to you on behalf of our mutual patient, Celia Johnson, a 26-month-old toddler currently under my care. Celia resides in Cambridge, MA, and we recently identified a plantar fascia injury in her left leg that necessitates further evaluation to determine the best course of action, including the possibility of surgery.

It is my belief that a consultation and thorough examination by a pediatric orthopedist are essential in this case. Children's musculoskeletal systems are constantly developing, making it especially important to provide specialized treatment and care for pediatric patients. Considering Celia's young age, the injury's impact on her growth, function, and quality of life must be carefully evaluated by an expert in pediatric orthopedics.

A pediatric orthopedist has the specialized training and experience necessary to diagnose and treat Celia's injury accurately. This expertise will allow them to determine the most effective and least invasive course of action. Prompt examination and intervention will minimize the risk of complications, avoiding potential long-term consequences and further medical costs associated with delayed or inappropriate treatment.

As Celia's primary care provider, I am acutely aware of the importance of this consultation to her overall health and well-being. I kindly request that you authorize a referral to a pediatric orthopedist for a comprehensive examination and evaluation. This step will play a vital role in ensuring Celia's healthy development and minimizing disruptions to her daily life.

Please do not hesitate to contact me if you require more information. I am confident that you will agree on the necessity of this consultation and examination, in the best interest of our patient, Celia Johnson. Your prompt attention to this matter is greatly appreciated.

Sincerely,

[Your Name]
[Your Title]
[Your Practice/Institution Name]

FIG. 18

SYSTEMS AND METHODS FOR ANONYMIZING PRIVATE DATA FOR USE IN MACHINE LEARNING MODELS

CROSS-REFERENCE TO RELATED APPLICATIONS

This application claims the benefit of U.S. Provisional Application No. 63/499,197 filed Apr. 28, 2023, and U.S. Provisional Application No. 63/509,516 filed Jun. 21, 2023, the entire contents of each of which are incorporated herein by reference for all purposes.

FIELD

This application relates generally to techniques for de-identifying and anonymizing private data included in machine learning models, from initial training to later inference. In particular, embodiments described herein include techniques for generating synthetic data to represent private data and mapping the private data to the synthetic data. A user request comprising the private data can be revised to include the synthetic data, with the revised user request being input to the trained external machine learning model.

BACKGROUND

Globally, many countries have enacted laws protecting its citizens' individual (i.e., private) data from being freely shared or utilized for commercial purposes. Upholding the strict legal requirements described and referred to in the United States' Health Insurance Portability and Accountability Act (HIPAA), which defines protections for Protected Health Information (PHI), as well as other privacy protection rules (e.g., European Union's General Data Protection Regulation (GDPR), personal information as defined in the California Consumer Privacy Act (CCPA), or similar protected data rules), is paramount to ensuring that one's private information remains confidential.

Patient information, such as that included in electronic health records, is one example of private data. While patient data is protected by legal provisions and cannot be used as-is due to privacy and security concerns, aggregate data such as statistics of patient populations, which cannot be traced back to a specific patient, can be used more freely by their owners (for example, healthcare providers) for a variety of reasons. Other known forms of information that can contain private and/or confidential data may include, but are not limited to, medical records, legal documents, educational records, criminal records, financial records, etc.

Today, machine learning models, such as large language models (LLMs), can be used to respond to task-specific requests. Owing to their large size and expensive training, the latest versions of such models reside on public computing environments, where security vulnerabilities (e.g., data leaks) can occur. Therefore, providing private information, such as protected health information (PHI), to a machine learning model in all phases of its development and use can compromise the confidentiality of the private information.

One technique to overcome this problem is to de-identify and/or anonymize the private information. However, existing techniques to de-identify and/or anonymize specific private information can, knowingly or unknowingly, strip away many aspects of the private information thereby rendering the de-identified and/or anonymized private information useless for clinical/functional applications.

Thus, what are needed are techniques that de-identify and/or anonymize data to a statistically and effectively untraceable level, while preserving a large portion of the data's clinical/functional applicability.

SUMMARY

Described herein are techniques for protecting confidential data, such as an individual's protected health information (PHI), from being publicly disclosed. Many countries around the world have taken steps to ensure that PHI is not freely shared or utilized for commercial purposes. Some example policies that have been developed to protect individuals' PHI include the Health Insurance Portability and Accountability Act (HIPAA), which defines protections of PHI. Some examples of PHI include a patient's name, age, injury or illness, medical images, medical history, insurance information, and the like.

An individual's PHI is generally stored electronically using an electronic health record (EHR). Policies like HIPAA set strict rules for who can access EHRs and what can be done with the PHI stored therein. However, aggregated data, such as health statistics regarding patient populations, is not subject to the same (if any) restrictions. Differing from PHI, the aggregated data can be shared more freely because the PHI cannot be connected back to specific individuals.

While techniques exist for de-identifying and anonymizing data, these techniques often strip away many crucial elements of the PHI. Therefore, even though the de-identified and anonymized data may not be traceable to a specific individual, it may be of little to no use for certain clinical/functional applications.

One such application is the use of artificial intelligence (AI) and machine learning (ML) models for responding to user requests. For example, AI can be used to predict medical outcomes, identify drug interactions, estimate survival rates, and many others. A user can specify the task or tasks to be performed by the AI via the user request. The request can be submitted to a computing environment where the AI/ML logic resides. However, these computing environments are often public and therefore susceptible to data leaks. Due to the potential for data leaks, leveraging AI/ML for tasks based on PHI can, unintentionally, result in publicly revealing an individual's PHI.

Described herein are techniques that overcome the aforementioned drawbacks by using synthetic PHI parameters in user requests to AI/ML instead of an individual's private PHI. The synthetic PHI parameters within responses produced by AI/ML to the user request can be replaced with the original PHI parameters. For example, a mapping of the original PHI parameters to the synthetic PHI parameters may be generated to revise the user request and the same mapping can be used to revise a response from the AI/ML. The synthetic PHI parameters can be generated based on the individual's PHI and patient population statistics such that they are statistically similar to the original PHI parameters. Thus, the present techniques can enable users to harness the power of AI/ML while ensuring that private data, such as an individual's personal PHI, remains protected.

In some embodiments, a method for performing a task using a trained machine learning model, is described. The method may include receiving a user request comprising the task and one or more protected health information (PHI) parameters associated with a patient. Using one or more trained machine learning models, the one or more PHI parameters associated with the patient can be extracted. The one or more trained machine learning model may be used to generate a revised user request by replacing the one or more PHI parameters in the user request with one or more synthetic PHI parameters. The revised user request may be provided to the trained external machine learning model, and a response to the task comprising the one or more synthetic PHI parameters may be received from the trained external machine learning model. The one or more trained machine learning models may generate a revised response to the task by replacing the one or more synthetic PHI parameters of the response with the one or more PHI parameters of the user request.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed can be resorted to by those skilled in the art, and that such modifications and variations are considered to be within the scope of this invention as defined by the appended claims.

BRIEF DESCRIPTION OF THE FIGURES

FIG. 3 illustrates an example user request, in accordance with various embodiments.

FIG. 5 illustrates an example data structure generated based on the example user request of FIG. 3, in accordance with various embodiments.

FIG. 10 illustrates an example revised user request, in accordance with various embodiments.

FIG. 14 illustrates an example mapping database, in accordance with various embodiments.

FIG. 16 illustrates an example response generated by a machine learning model based on a revised user request comprising synthetic PHI parameters, in accordance with various embodiments.

FIG. 18 illustrates an example revised response, in accordance with various embodiments.

DETAILED DESCRIPTION

Figure 1:
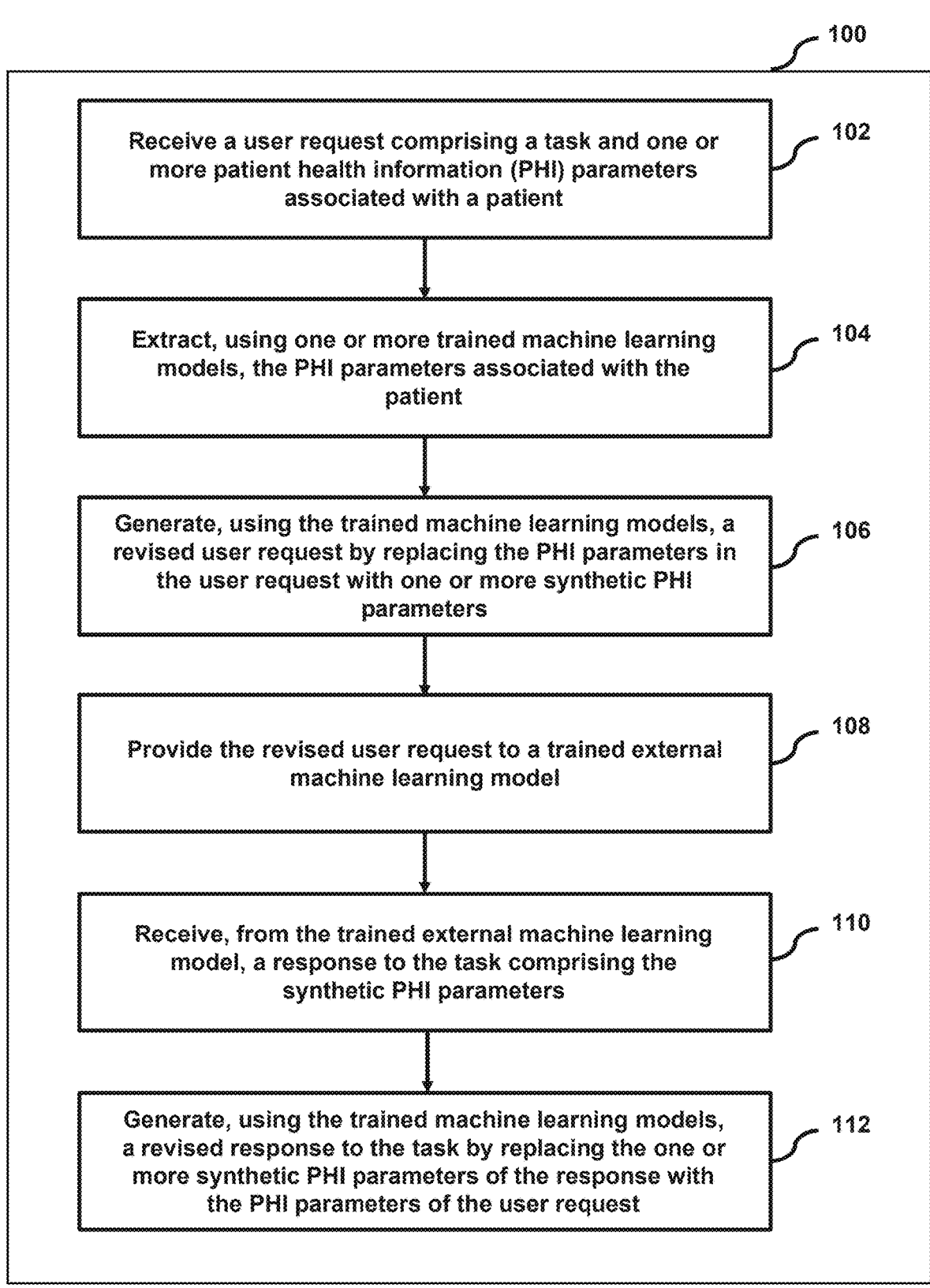
FIG. 1 illustrates an example method for performing a task using a machine learning model, in accordance with various embodiments.

Described herein are systems, methods, and programming describing techniques for de-identifying and/or anonymizing private data. The de-identified and anonymized data can be used when interacting with trained external models without risking the confidentiality of the private data. In particular, private data included in a user request to a trained external model, which may be public, private, or a combination thereof, such as some large language models (LLMs), may be replaced with synthetic data. The synthetic data may be designed such that it cannot be traced back to a specific individual. For example, the synthetic data may be generated based on the private data and patient population statistics.

The techniques described herein overcome the problems of existing de-identification and anonymization processes, which strip away many crucial aspects of the data. In particular, the techniques described herein can de-identify and anonymize the private data so that it cannot be traced back to a specific individual, while also ensuring that the data is useful for practical applications.

Many jurisdictions around the world have taken steps to ensure that PHI is not freely shared or utilized for commercial purposes. Some example policies that have been developed to protect individuals' PHI include, in the United States, the Health Insurance Portability and Accountability Act (HIPAA), which defines protections PHI. In Europe, the European Union's General Data Protection Regulation (GDPR) serves a similar purpose. Policies like HIPAA and GDPR set strict rules for who can access these electronic health records (EHRs) storing PHI and what can be done with the PHI stored therein. Some examples of PHI include a patient's name, age, injury or illness, medical images, medical history, insurance information, and the like.

Machine learning (ML) models can be used to predict medical outcomes, identify drug interactions, estimate survival rates, and many others. A user can specify the task or tasks to be performed by the via a user request. The request can be submitted to a computing environment where the ML model's logic resides. A user can access the model using a client device, submit the request, and receive a response to the request. However, public computing environments, such as those within which an ML model can operate, are known to have a greater risk of security threats (e.g., data leaks, breeches, etc.). Therefore, transmitting an individual's private PHI to a public computing environment risks exposing that data.

The techniques described herein replace private PHI parameters included within a user request to an external machine learning model with synthetic PHI parameters. These synthetic PHI parameters are statistically similar to the original PHI parameters, but are not traceable back to a specific individual. In some examples, a mapping of the original PHI parameters to the synthetic PHI parameters may be generated and stored in memory. After the ML model generates a response, the mapping can be leveraged to replace the synthetic PHI parameters with the original PHI parameters, and the revised response can then be output. Thus, the ML model's computing environment never receives the original PHI parameters, but still is capable of performing the desired task with statistically similar synthetic PHI parameters.

The synthetic PHI parameters can be generated based on the individual's PHI and patient population statistics. The patient population statistics, which aggregate health-related information from a large population of individuals to identify trends, is not able to be traced back to specific individuals. This aggregated data, such as health statistics regarding patient populations, is not subject to the same privacy protection restrictions (e.g., HIPAA, GDPR). Differing from PHI, the aggregated data can be shared more freely because the PHI cannot be connected back to specific individuals. The patient population statistics for example allows the system to understand how relevant a given PHI parameter is to the request and how to generate a synthetic PHI parameter that is statistical relevant to the original PHI parameter.

In some embodiments, a user request comprising the task and protected health information (PHI) parameters associated with a patient may be received at a computing system. For example, the user request may comprise a prompt to be input to a trained external machine learning model. In one or more examples, the trained external machine learning model may reside in a public computing environment. Inputting the PHI parameters to the trained external machine learning model can compromise the confidentiality of the private information described by the PHI parameters.

As described herein, an external machine learning model may include machine learning models, machine learning-based software modules, products, services that are available to receive queries, and the like. In some embodiments, the external machine learning model may be deployed on a public computing environment, a private computing environment, or a hybrid environment. A public computing environment is unrestricted, and therefore can be accessed by any compatible device. A private machine learning model refers to a machine learning model operating within a private computing environment. A private computing environment employs restrictions, and therefore not all devices are allowed to access it. Hybrid computing environments employ certain restrictions/requirements to use the network, but are generally accessible by devices.

In some embodiments, one or more trained machine learning models may extract the PHI parameters associated with the patient from the user request. The PHI parameters may include information such as a patient name, a health record identifier, an age of the patient, a type of injury or illness the patient has, an affected body part or parts, patient insurance information, or other information.

In some embodiments, the trained machine learning models may be used to generate a revised user request. The revised user request may include one or more synthetic PHI parameters. The synthetic PHI parameters may replace the corresponding PHI parameters within the user request. The synthetic parameters may be generated by retrieving clinical relevance data indicating how relevant each of the PHI parameters are to a task specified by the user request and modifying the extracted PHI parameters based on the clinical relevance data. The revised user request can be provided to the trained external machine learning model (e.g., a large language model (LLM)), operating on a public computing environment, without fear that the private PHI parameters will be exposed (e.g., via data breaches/leaks).

The trained external model may be configured to output a response to the revised user request. The response may include the synthetic PHI parameters, which were included within the revised user request input to the trained external machine learning model. The trained machine learning models may generate and store a mapping between the extracted PHI parameters and the generated synthetic PHI parameters. The trained machine learning models may replace the generated synthetic PHI parameters with the corresponding extracted PHI parameters based on the mapping, and the revised user response may be output to a requesting client device and/or stored in a user request/response database.

While described with respect to health information, the present disclosure can be applied similarly for non-medical data, such as, for example, legal information, education information, financial information, and the like.

FIG. 1 is an illustrative flowchart of an example process 100 for performing a task using a trained external machine learning model, in accordance with various embodiments. Process 100 may be performed using a computing system comprising one or more processors, memory storing computer program instructions, and/or other components. In some embodiments, process 100 may be in communication with one or more databases, user devices, computing systems (e.g., servers), and the like. In one or more examples, process 100 may begin at step 102.

At step 102, a user request comprising a task and one or more protected health information (PHI) parameters associated with a patient may be received. At step 104, the one or more PHI parameters associated with the subject may be extracted using one or more trained machine learning models. At step 106, a revised user request may be generated using the trained machine learning models by replacing the PHI parameters in the user request with one or more synthetic PHI parameters. At step 108, the revised user request may be provided to a trained external machine learning model. At step 110, a response to the task may be received from the external trained machine learning model, where the response comprises the one or more synthetic PHI parameters. At step 112, a revised response to the task may be generated using the trained machine learning models by replacing the one or more synthetic PHI parameters with the one or more PHI parameters.

Figure 2:
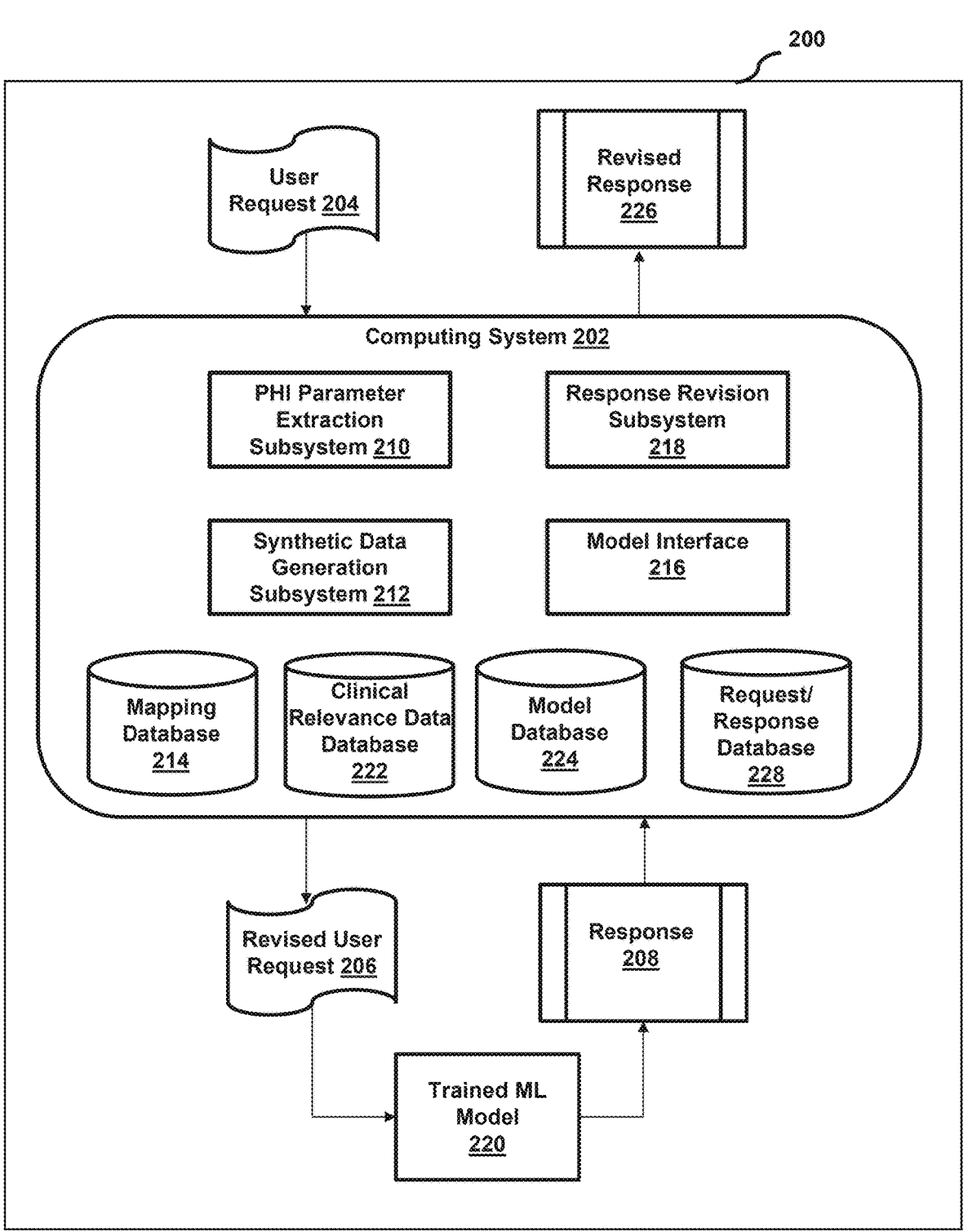
FIG. 2 illustrates an example system for performing a task using a machine learning model, in accordance with various embodiments.

As an example, with reference to FIG. 2, a user request 204 may be provided to a computing system 202. In some embodiments, computing system 202 may include a protected health information (PHI) parameter extraction subsystem 210, a synthetic data generation subsystem 212, a model interface 216, a response revision subsystem 218, or other components. For example, computing system 202 may include, or be in communication with, one or more databases (e.g., mapping database 214, clinical relevance data database 222, model database 224), or other devices, systems, servers, etc. Computing system 202 may be implemented as an intermediate layer between a client device and a model 220. In some embodiments, a user may submit user request 204 via their client device, and user request 204 may be input to computing system 202. Computing system 202 may be configured to perform one or more actions to de-identify and anonymize private data included within user request 204. For example, user request 204 may include private protected health information associated with the patient, such as the patient's name, date of birth, insurance information, injury/ illness, and the like. User request 204 may also include or reference confidential medical records, such as medical images, lab work, medical history, etc.

In some embodiments, user request 204 may indicate a task to be performed by model 220. In one or more examples, the task may be explicitly defined within user request 204. For example, as seen with reference to FIG. 3, user request 204 may include text specifying a task to be performed by model 220 (e.g., "Create a medical recommendation for Celia Johnson to be seen by a pediatric orthopedist"). Alternatively, or additionally, an application programming interface (API) of model 220 may allow present selectable options (e.g., drop-down screens) for controlling the contents of user request 204.

In some cases, computing system 202 may be configured to determine the task by analyzing user request 204. For example, computing system 202 may implement one or more machine learning models (e.g., natural language processing models, computer vision models, etc.) trained to extract private data from user request 204, generate synthetic data representing the private data, generate a revised user request 206 including the synthetic data replacing some or all of the private data, and providing revised user request 206 to trained ML model 220.

In one or more examples, user request 204 comprises text. As seen with reference to FIG. 3, user request 204 may comprise text. For example, the text may recite:
"Celia Johnson, MRN 12033313, from Cambridge, MA is a 26-month-old toddler had a plantar fascia injury in her left leg and we need to decide on whether to operate or not. Write a letter to her insurer, Insurance A, that would justify a thorough examination by a pediatric orthopedist."

As seen in the example of FIG. 3, certain words, phrases, and/or character strings may be underlined. Each underlined item may represent a PHI parameter. For example, the text may include the PHI parameters: "Patient Name," "Medical Record Number," "Location," "Age," "Injury," "Body Part," "Insurer," having values "Celia Johnson," "MRN 12033313," "Cambridge, MA," "26-months-old," "Plantar Fascia," "Left Leg," and "Insurance A," respectively.

In one or more examples, user request 204 comprises one or more images and/or videos. Still further, in some examples, user request 204 may include other types of data, such as plots, charts, audio, spreadsheets, or combinations thereof. Depending on the type of data included in user request 204, different models may be used to extract the PHI parameters. For example, for user request 204 as illustrated in FIG. 3, one or more natural language processing (NLP) models may be used to extract the PHI parameters from the text. As another example, one or more computer vision models may be used to extract the PHI parameters from the images/videos.

Returning to FIG. 2, in some embodiments, model 220 may be trained to generate a response 208. Response 208 may be created based on the identified task or tasks indicated by revised user request 206. For example, if the task is "Create a medical recommendation for Celia Johnson to be seen by a pediatric orthopedist," then response 208 may comprise a written document. In some embodiments, model 220 is a trained external machine learning model, such as a large language model (LLMs). In some examples, model 220 resides on a public computing environment. In some embodiments, computing system 202 may serve as an intermediate layer between a client device and model 220. In some embodiments, computing system 202 is a client device that interacts with model 220. For example, the functionalities of computing system 202 may be implemented locally on a client device (e.g., smart phone, tablet, personal computer, wearable device, etc.).

Response 208 may include some or all of the synthetic data generated by computing system 202. For example, response 208 may have the PHI parameter "Patient Name" populated with the name "Talia Ferber" based on revised user request 206. If user request 204 had been used instead of revised user request 206, then the PHI parameter "Patient Name" (e.g., "Celia Johnson") would have exposed to the public computing environment of model 220. Instead, the name "Talia Ferber," synthetically generated by computing system 202, is provided to model 220. Thus, even model 220 is subject to a data leak, the private PHI information (e.g., the name "Celia Johnson") remains protected and private.

Computing system 202 may be configured to generate and output a revised response 226 based on response 208 and a mapping of private data to synthetic data. Thus, continuing the example above, computing system 202 may generate revised response 226 having the name "Celia Johnson" replace any instance of the name "Talia Ferber" within response 208. Similar steps may also be taken for other PHI parameters (e.g., "Patient Location," "Insurer," etc.).

Returning to step 104 of FIG. 1, the one or more PHI parameters associated with the subject may be extracted using one or more trained machine learning models. In some embodiments, the PHI parameters comprise at least one of: "Patient Name," "Patient Injury," "Patient Illness," "Patient Age," "Body Part," "Patient Medical Record Number," "Patient Insurer," or other protected health information, or combinations thereof. In one or more examples, the PHI parameters may include "Patient Location," "Patient Address," "Patient Contact Information," "Patient Billing Information," and the like.

Figure 4:
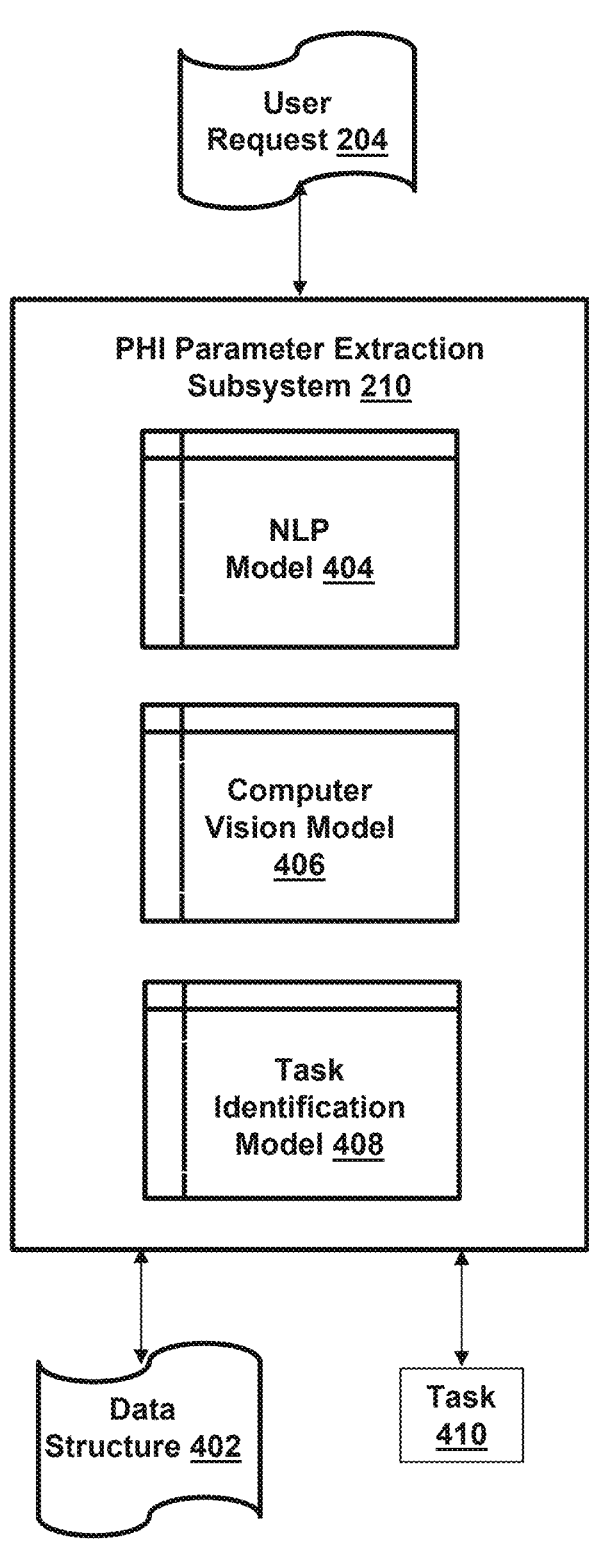
FIG. 4 illustrates an example PHI parameter extraction subsystem, in accordance with various embodiments.

In some embodiments, PHI parameter extraction subsystem 210 of computing system 202 may be configured to extract the PHI parameters associated with the subject. With reference to FIG. 4, PHI parameter extraction subsystem 210 may be configured to receive user request 204, generate a data structure 402, and determine a task that is being request, via user request 204, to be performed by model 220. Data structure 402 may comprise a plurality of data fields that can be populated with values extracted from user request 204. Each data field may correspond to a PHI parameter, and the extract text, objects, or other data from user request 204 may be used to populate the value of that data field. As an example, with reference to FIG. 5, data structure 402 may include a plurality of data fields corresponding to one or more PHI parameters (e.g., "Patient Name," "Medical Record Number," "Location," "Age," "Injury," "Body Part,"

"Insurer"). Each data field may have a corresponding value. For example, the data field in data structure 402 corresponding to the PHI parameter "Patient Name" may be populated with the value "Celia Johnson" extracted from the text of user request 204. Similarly, the data field in data structure 402 corresponding to the PHI parameter "Location" may be populated with the value "Cambridge, MA" extracted from the text of user request 204.

In some embodiments, one or more pieces of supplemental data may be obtained by PHI parameter extraction subsystem 210. For example, the patient may be identified and, based on the identification, one or more electronic health records, or other private data, may be retrieved from one or more databases. The supplemental data may be used to cross-reference the PHI parameters detected within user request 204, as well as determine additional PHI parameters that may be included within revised user request 206 to improve an accuracy of response 208 produced by model 220.

In some embodiments, PHI parameter extraction subsystem 210 may implement one or more trained machine learning models, such as a natural language processing (NLP) model 404. In some embodiments, user request 204 may comprise text. In one or more examples, the text may be input to NLP model 404 to obtain the one or more PHI parameters associated with the patient. NLP model 404 may be trained to populate data structure 402 representing user request 204 based on the text. In some embodiments, process 100 may include a step of providing the text to NLP model 404. For example, PHI parameter extraction subsystem 210 may be configured to receive user request 204 and input user request 204 to NLP model 404. In some embodiments, NLP model 404 may be trained to parse the text into a plurality of text tokens, determine which, if any, text tokens correspond to a particular PHI parameter. NLP model 404 may populate data fields of data structure 402 associated with each PHI parameter with the corresponding text tokens (e.g., using semantic information associated with the text, part-of-speech recognition, entity resolution, etc.). The text tokens populated to the data fields may comprise the PHI parameters.

In some embodiments, process 100 may include a step of providing the one or more images included in user request 204 to computer vision model 406. Computer vision model 406 may be trained to detect one or more objects within at least one of the one or more images, determine, based on the one or more detected objects, one or more data fields associated with each of the objects, and populate the data fields of data structure 402 with an indication of the one or more detected objects. In one or more examples, data structure 402 represents user request 204 and comprises the one or more data fields. The data fields may be populated with values indicated the detected objects. In some embodiments, the values indicating the detected objects may comprise the PHI parameters.

In some embodiments, the trained machine learning models implemented by PHI parameter extraction subsystem 210 may include a computer vision model 406. In some embodiments, user request 204 comprises one or more images. In one or more examples, the one or more images may be input to computer vision model 406. Computer vision model 406 may be trained to scan the images and determine whether any known objects are present. If so, computer vision model 406 may output indications of each detected object. In some examples, the output indications and/or the detected objects may comprise the extracted PHI parameters. In some embodiments, computer vision model 406 may be trained to populate data structure 402 representing user request 204 with the output indications and/or detected objects. For example, data structure 402 may include data fields corresponding to PHI parameters, and each data field may store a value extracted by computer vision model 406.

In some embodiments, PHI parameter subsystem 210 may be configured to implement NLP model 404 and computer vision model 406 to analyze user request 204. For example, user request 204 may include images depicting objects. Computer vision model 406 may analyze the images to detect the objects and determine information about the object (e.g., object name, object quantity, object location within the image, etc.).

In some embodiments, PHI parameter subsystem 210 may be configured to implement a task identification model 408 to determine a task that has been request by user request 204 to be performed by model 220. Task identification model 408 may determine the task based on extracted PHI parameters. In one or more examples, the extracted PHI parameters may be stored as the values populating the data fields of data structure 402.

In some embodiments, these extracted PHI parameters may be used to determine an intent of user request 204. The intent may serve as a basis for a task requested to be performed by model 220. In one or more examples, task identification model 408 may query a task/intent database to determine a most-likely task associated with the intent of user request 204. In some embodiments, process 100 may include a step of determining an intent of the user request based on the one or more populated data fields of data structure 402. For example, NLP model 404 and/or computer vision model 406 may be trained to estimate an intent of user request 204 based on the values populated to each of the data fields. In one or more examples, the task to be performed by model 220 may be based on the intent.

Figure 6:
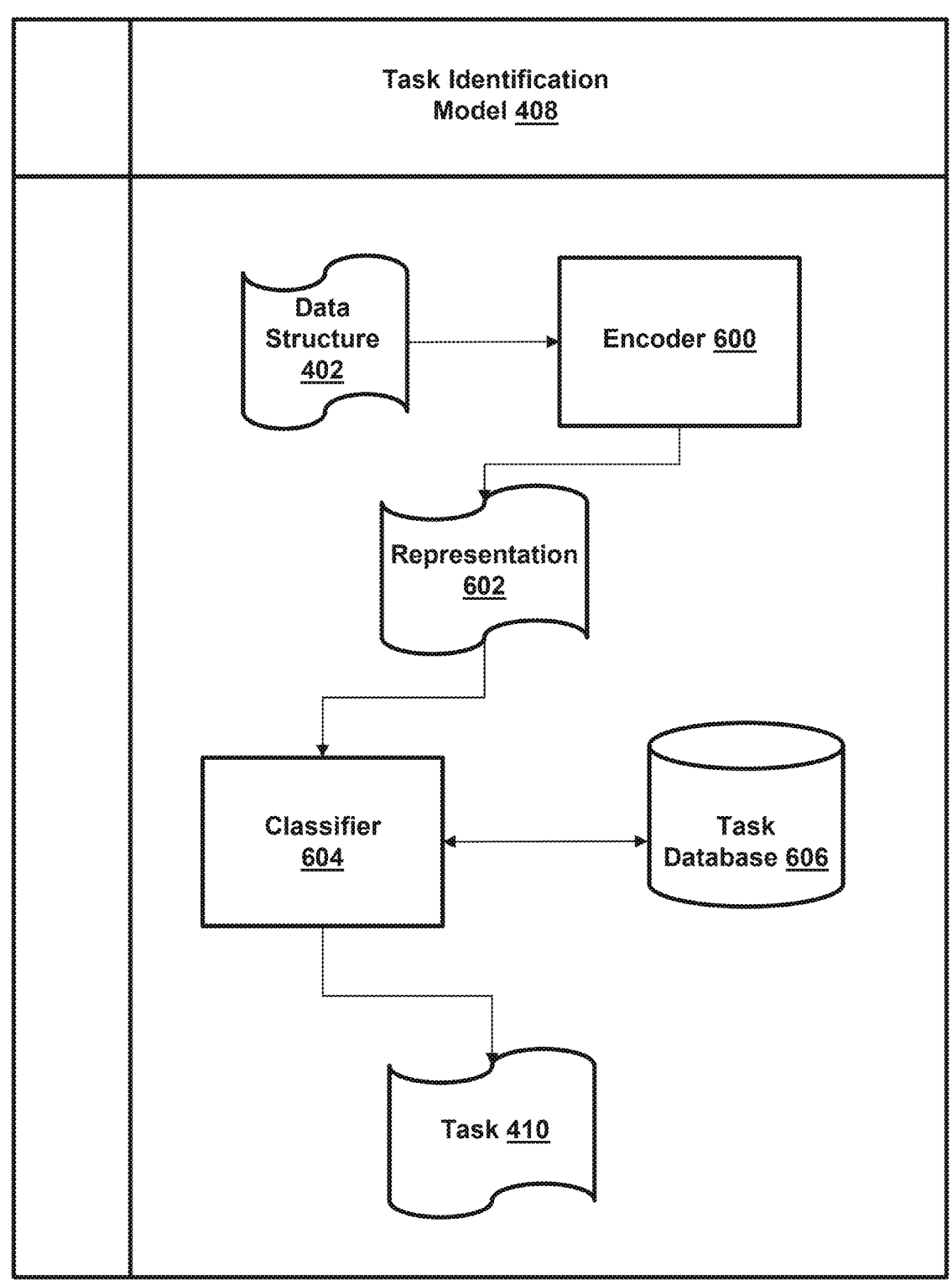
FIG. 6 illustrates an example task identification model, in accordance with various embodiments.

In some embodiments, task identification model 408 may be trained to determine a task 410 requested by user request 204 based on data structure 402. As an example, with reference to FIG. 6, task identification model 408 may input data structure 402 into an encoder 600. Encoder 600 may be trained to generate a representation 602 of user request 204. In some embodiments, representation 602 may comprise an embedding. Representation 602 may include N elements, where each element may correspond to a value of a data field of data structure 402 associated with one of the one or more extracted PHI parameters. In some embodiments, representation 602 may be input to a classifier 604. Classifier 604 may be trained to determine a task associated with representation 602. In one or more examples, classifier 604 may query a task database 606 to determine task 410. In some embodiments, classifier 604 may compute a similarity between representation 602 and a representation of previously received user requests. As an example, the similarity may be computed based on a distance between representation 602 and the representation of each previously received user request. Task 410 may be determined by classifier 604 based on the distances. For example, classifier 604 may select task 410 from a plurality of possible tasks stored in task database 606 based on the distance between representation 602 and a representation of task 410 being smallest as compared to all other possible tasks. As another example, classifier 604 may select task 410 based on the similarity score computed by classifier 604 between representation 602 and the representation of task 410 being less than a threshold distance. The distance metrics used to compute the similarity score may include, but are not limited to, an L2 distance, a Manhattan distance, and/or a Cosine distance.

Figure 7:
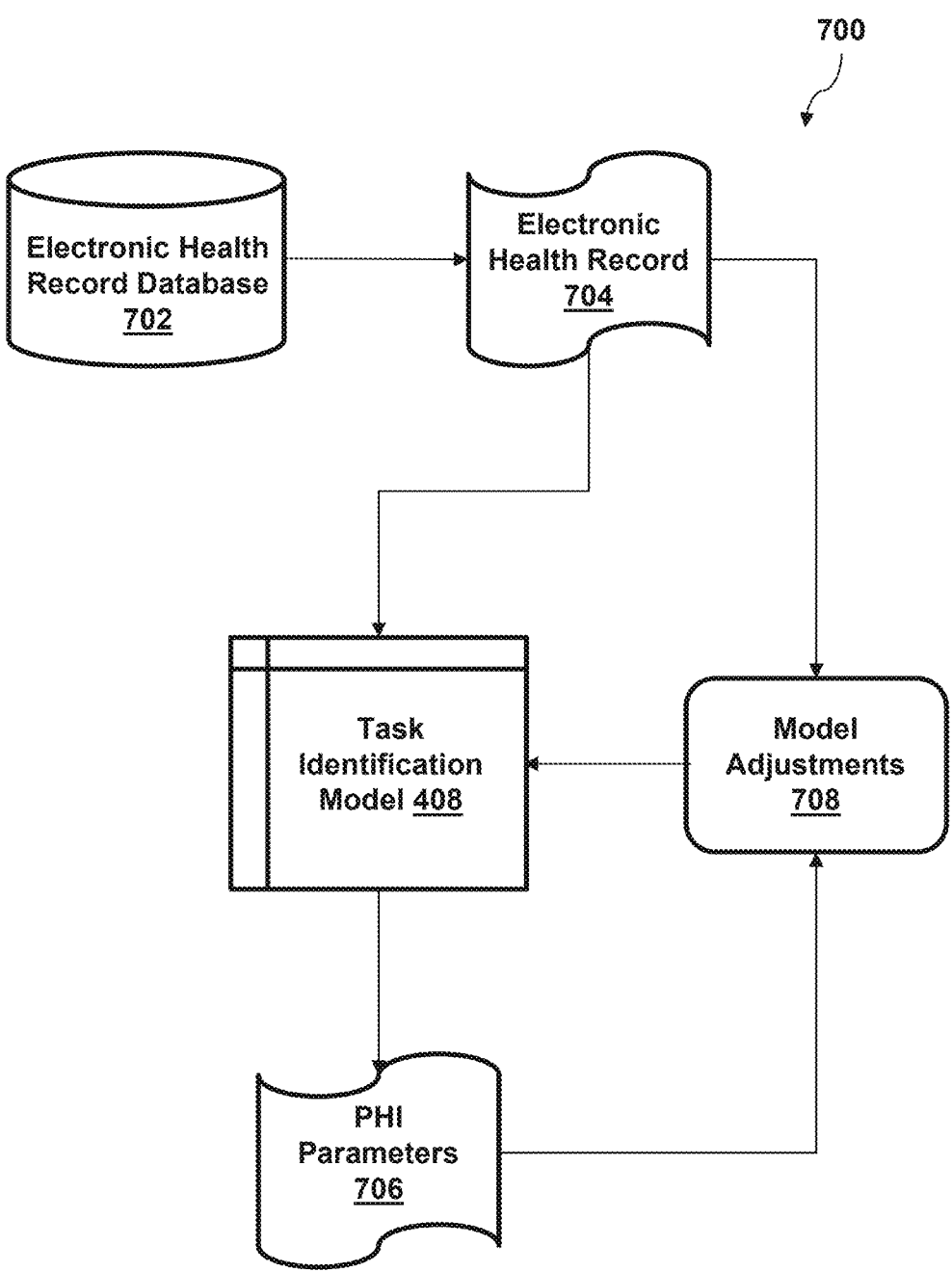
FIG. 7 illustrates an example training process for training a task identification model, in accordance with various embodiments.
Figure 8:
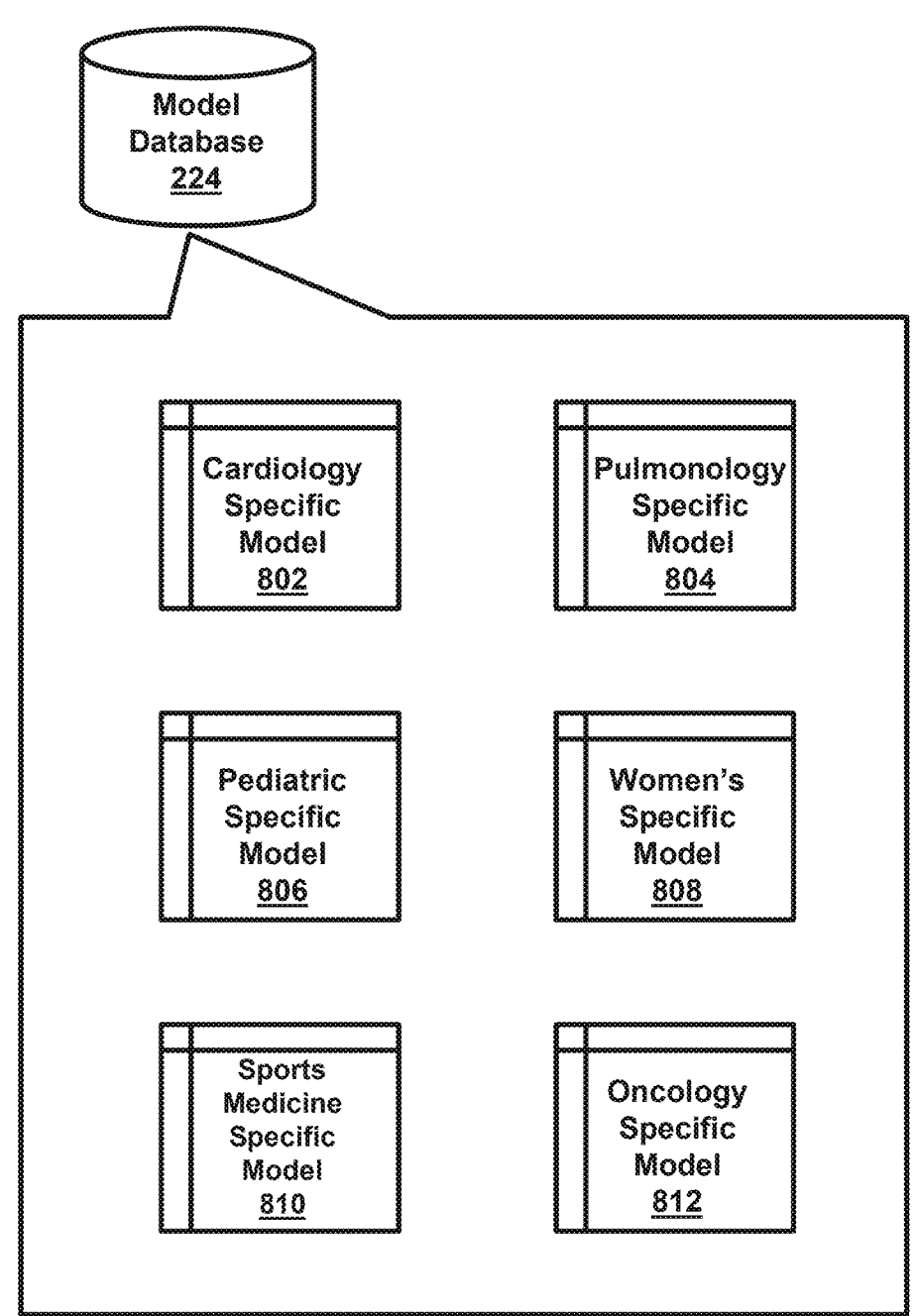
FIG. 8 illustrates an example model database storing medical-condition-specific machine learning models, in accordance with various embodiments.

In some embodiments, process 100 may include a step of training one or more machine learning models using a corpus of electronic health records (EHRs) of a plurality of subjects. As an example, a training process 700 of FIG. 7 can be used to train task identification model 408. Training process 700 may produce models that are trained for specific medical conditions/injuries/subjects, indicating the most likely PHI parameters model 220 needed to generate a revised user request that produces an accurate response without exposing private data to a public computing environment. FIG. 8 illustrates an example of model database 224 storing trained models, such as cardiology-specific model 802, pulmonology-specific model 804, pediatric-specific model 806, women's-specific model 808, sports medicine-specific model 810, oncology-specific model 812, or other models. Each model may relate to a particular medical condition and a medical-condition-specific set of PHI parameters.

Returning to FIG. 7, EHR database 702 may include health records of a number of different subjects of various ages, with a variety of injuries and/or illness. For example, EHR database 702 may store health records of patients having different medical conditions, such as, but not limited to, cardiological conditions, pulmonary conditions, pediatric conditions, women's health conditions, sports medicine conditions, various cancers, or other illness/injuries, or combinations thereof. Model database 224 may store the trained machine learning models, which may be trained for specific medical conditions. As mentioned above with reference to FIG. 8, model database 224 may include trained medical-condition-specific machine learning models, such as: cardiology-specific model 802 trained on EHRs stored in EHR database 702 of patients diagnosed with one or more cardiological conditions, pulmonary-specific model 804 trained on EHRs stored in EHR database 702 of patients diagnosed with one or more pulmonary conditions, pediatric-specific model 806 trained on EHRs stored in EHR database 702 of patients having one or more pediatric conditions, women's-health-specific model 808 trained on EHRs stored in EHR database 702 of patients having one or more women's-health conditions, sport-medicine-specific model 810 trained on EHRs stored in EHR database 702 of patients having one or more sports-medicine conditions, and/or oncology-specific model 812 trained on EHRs stored in EHR database 702 of patients having one or more forms of cancers.

In some embodiments, training process 700 may include one or more electronic health records 704 being retrieved from EHR database 702. Health records 704 may each correspond to a particular medical condition such that task identification model 408 will be trained to determine PHI parameters for that medical condition. For example, health records 704 may relate to subjects having cardiological conditions. In this example, task identification model 408 can be implemented using cardiology-specific model 802. In this scenario, task identification model 408 may be trained to predict PHI parameters 706, which can be used to generate synthetic PHI parameters for revised user request 206 to be input to model 220.

In some embodiments, task identification model 408 may use multiple medical-condition-specific models. For example, user request 204 may relate to pediatric oncology, and task identification model 408 may include aspects from pediatric-specific model 806 and oncology-specific model 812. In this example, task identification model 408 may be trained using EHRs 704 of subjects having pediatric cancer, and may predict PHI parameters 706 that are relevant to generating responses from model 220.

In some embodiments, task identification model 408 may be configured to receive EHRs 704 and output a prediction of PHI parameters 706. In one or more examples, each of EHRs 704 may also include a list of predetermined model-specific PHI parameters associated with a medical condition for which task identification model 408 is being trained. For example, if task identification model 408 is to be trained to predict PHI parameters for a patient having a cardiology condition, EHRs 704 may include a list of known PHI parameters that are relevant when submitting user requests to model 220 to generate task-specific responses (e.g., response 208).

Training process 700 may also include a step whereby one or more adjustments 708 are made to one or more hyperparameters of task identification model 408. For example, predicted PHI parameters 706 may be compared to the list of known PHI parameters to compute a loss. The loss defines how well task identification model 408 predicted PHI parameters 706. In some embodiments, different optimization techniques known to those of ordinary skill in the art may be used to optimize hyperparameter tunings (e.g., the Adam optimizer).

Training process 700 may repeat a predefined number of times and/or until task identification model 408 predicts PHI parameters 706 with an accuracy greater than or equal to a threshold accuracy. In some embodiments, EHRs 704 from EHR database 702 may be split into training, validation, and testing data. During training, the hyperparameters of task identification model 408 may be adjusted. Upon testing and validation indicating that task identification model 408 can predict PHI parameters 706 with an accuracy greater than or equal to the threshold accuracy (e.g., 80% or greater accuracy, 90% or greater accuracy, 95% or greater accuracy, etc.), task identification model 408 can be stored within model database 224 for deployment by computing system 202 (e.g., when processing user request 204).

In one or more examples, each of the specialized machine learning models (e.g., the models stored in model database 224) may include a model-specific set of PHI parameters associated with a corresponding medical condition. For example, cardiology-specific model 802 may include a cardiology-specific set of PHI parameters which may be derived from an input user request (e.g., user request 204), pulmonology-specific model 804 may include a pulmonology-specific set of PHI parameters which may be derived from an input user request, pediatric-specific model 806 may include a pediatric-specific set of PHI parameters which may be derived from an input user request, women's-specific model 808 may include a women's-specific set of PHI parameters which may be derived from an input user request, sports medicine-specific model 810 may include a sports medicine-specific set of PHI parameters which may be derived from an input user request, and oncology-specific model 812 may include an oncology-specific set of PHI parameters which may be derived from an input user request.

Some example PHI parameters include, but are not limited to, names, geographic subdivisions smaller than a state, including street address, city, county, precinct, zip code, and their equivalent geocodes, except for the initial three digits of a zip code if, according to the current publicly available data from the Bureau of the Census, the geographic unit formed by combining all zip codes with the same three initial digits contains more than 20,000 people, and the initial three digits of a zip code for all such geographic units containing 20,000 or fewer people is changed to 000. Additional example PHI parameters include: all elements of dates (except year) for dates directly related to an individual, including birth date, admission date, discharge date, date of death; and all ages over 89 and all elements of dates (including year) indicative of such age, except that such ages and elements may be aggregated into a single category of age 90 or older; telephone numbers; fax numbers; electronic mail addresses; social security numbers; medical record numbers; health plan beneficiary numbers; account numbers; certificate/license numbers; vehicle identifiers and serial numbers, including license plate numbers; device identifiers and serial numbers; web Universal Resource Locators (URLs); Internet Protocol (IP) address numbers; biometric identifiers, including finger and voice prints; full face photographic images and any comparable images; and any other unique identifying number, characteristic, or code. Still further, some example PHI parameters include combinations of medical conditions that fewer than 20,000 people have; specific medical tests and their dates; test results data; x-rays (particularly head); skin/face/hand photos; or body measurements.

Figure 9:
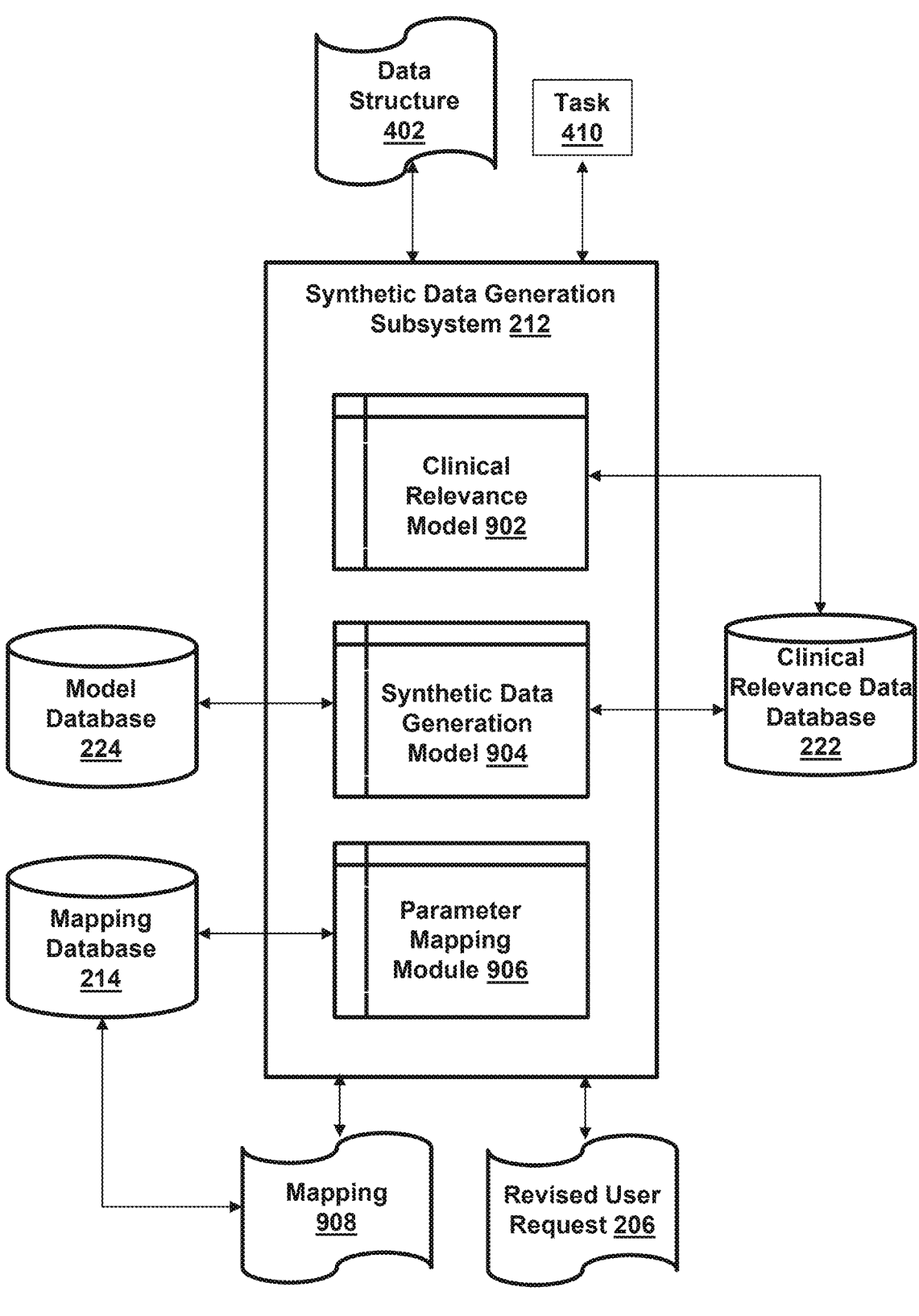
FIG. 9 illustrates an example synthetic data generation subsystem, in accordance with various embodiments.

Returning to step 106 of FIG. 1, a revised user request may be generated using the trained machine learning models by replacing the PHI parameters in the user request with one or more synthetic PHI parameters. As an example, with reference to FIG. 9, synthetic data generation subsystem 212 may be configured to generate revised user request 206 based on data structure 402, task 410, other information (e.g., clinical relevance data associated with the task), or combinations thereof. As seen FIG. 9, synthetic data generation subsystem 212 may implement a clinical relevance model 902, a synthetic data generation model 904, or other models, and may include a parameter mapping module 906, or other components.

In some embodiments, process 100 may include a step of generating the synthetic PHI parameters based on the extracted PHI parameters and clinical relevance data associated with the task. In one or more examples, the clinical relevance data comprises a model-specific set of PHI parameters associated with the task and a relevancy score indicating how relevant each of the model-specific PHI parameters is to the task to be performed by model 220. With reference again to FIG. 3, user request 204 may include PHI parameters: "Patient Name," "Medical Record Number," "Location," "Age," "Injury," "Body Part," "Insurer," having values "Celia Johnson," "MRN 12033313," "Cambridge, MA," "26-months-old," "Plantar Fascia," "Left Leg," and "Insurance A," respectively.

Synthetic data generation model 904 may generate synthetic PHI parameters, as described herein. For example, the synthetic PHI parameters "Patient Name," "Medical Record Number," "Location," "Age," "Injury," "Body Part," "Insurer," may have the values: "Talia Ferber," " ", "Boston, MA," "36-months-old," "Plantar Fascia Injury," "Insurance B," respectively. For example, as seen in 908, revised user request 206 may include synthetic PHI parameters replacing some or all of the PHI parameters (e.g., underlined text in FIG. 3). In some embodiments, the synthetic PHI parameters may be selected and generated based, at least in part, on clinical relevance data associated with the identified task. In the example of FIG. 10, some of the PHI parameters have been replaced with their synthetic PHI parameters. For example, the PHI parameter "Patient Age" has a value of "26-months-old" in user request 204 and is replaced with the synthetic PHI parameter value "36-months-old" in revised user request 206. In one or more examples, some of the values of the synthetic PHI parameters may be the same as the values of the PHI parameters. For example, the PHI parameter "Injury" may have a value "Plantar Fascia Injury," which may be equal to the synthetic PHI parameter. In one or more examples, some of the synthetic PHI parameters may not be used in revised user request 206, however they may be nonetheless stored as metadata within data structure 402 for input to model 220. Doing so may allow model 220 to formulate response 208 including synthetic PHI parameters even if not all of those synthetic PHI parameters are included in revised user request 206.

In some embodiments, clinical relevance model 902 may be trained to determine a clinical relevance data most-closely associated with user request 204 based on data structure 402 and task 410. In some embodiments, process 100 may include a step of encoding the PHI parameters including some or all of the PHI parameters that have been modified. In one or more examples, the synthetic PHI parameters comprise the encoded PHI parameters.

In some embodiments, the trained machine learning models comprise an encoder. The encoder may be trained to generate a representation of the user request in a multi-dimensional feature space. In one or more examples, the encoder may generate an embedding representing the user request and the feature space comprises an embedding space. In some embodiments, process 100 may include a step of inputting the user request to the encoder to obtain an encoded representation of the user request. For example, the encoded representation may be an embedding representing the user request.

Figure 11:
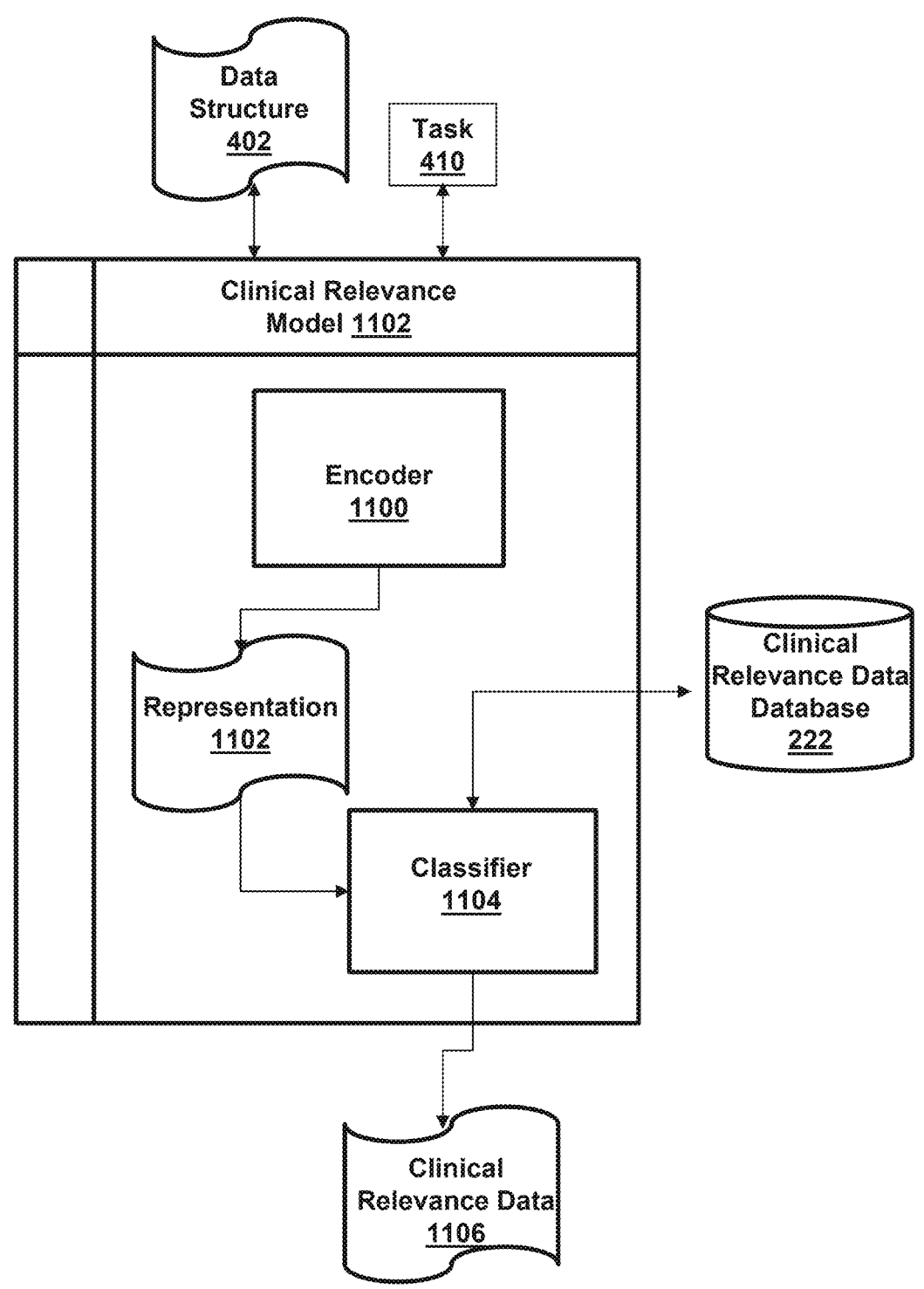
FIG. 11 illustrates an example clinical relevance model, in accordance with various embodiments.

As an example, with reference to FIG. 11, clinical relevance model 902 may input data structure 402 and task 410 into an encoder 1100. Encoder 1100 may be trained to generate a representation 1102 of data structure 402 and task 410. An embedding is a vector representation of the user request comprising PHI parameters. The embedding captures rich semantic information of the user request (e.g., tasks, private/confidential data, etc.), while excluding information that is not relevant to downstream analyses. The embedding can be a vector representation of the user request in the latent space. Translating the user request into an embedding can significantly reduce the size and dimension of the original data. The lower-dimension embedding can be used for downstream processing, as described herein. In some embodiments, representation 1102 may comprise an embedding. Representation 1102 may include M elements, where each element may correspond to a value of a data field of data structure 402 and at least one data field for task 410.

Process 100 may further include a step of computing a similarity score between the encoded representation and a plurality of encoded representations each associated with one of a plurality of previous user requests. In some embodiments, representation 1102 may be input to a classifier 1104. Classifier 1104 may be trained to determine clinical relevance data 1106 associated with representation 1102. In one or more examples, classifier 1104 may clinical relevance data database 222 to determine clinical relevance data 1106. In some embodiments, classifier 1104 may compute a similarity between representation 1102 and a representation of previously received user requests. As an example, the similarity may be computed by computing a distance between representation 1102 and the representation of each previously received user request's corresponding data structure and identified task.

Process 100 may still further include a step of identifying one or more of the plurality of previous user requests based on the ranking, wherein the clinical relevance data is selected from a clinical relevance database based on the one or more of the plurality of previous user requests. Clinical relevance data 1106 may be determined by classifier 1104 based on the distances. For example, classifier 1104 may select clinical relevance data 1106 from a plurality of different clinical relevance data associated with different types of tasks and different values of the data fields stored within data structure 402 based on the distance between representation 1102 and a representation of clinical relevance data 1106 being smallest as compared to all other possible tasks. As another example, classifier 1104 may select clinical relevance data 1106 based on the similarity score computed by classifier 1104 between representation 1102 and the representation of clinical relevance data 1106 being less than a threshold distance. The distance metrics used to compute the similarity score may include, but are not limited to, an L2 distance, a Manhattan distance, and/or a Cosine distance.

In some embodiments, representation 1102 may be input to a classifier 1104. Classifier 1104 may be trained to determine clinical relevance data 1106 associated with representation 1102. In one or more examples, classifier 1104 may clinical relevance data database 222 to determine clinical relevance data 1106. In some embodiments, classifier 1104 may compute a similarity between representation 1102 and a representation of previously received user requests. As an example, the similarity may be computed by computing a distance between representation 1102 and the representation of each previously received user request's corresponding data structure and identified task.

In one or more examples, the one or more of the plurality of previous user requests are identified based on the distance between the embedding and an embedding of the plurality of embeddings corresponding to the one or more of the plurality of previous user requests being less than a threshold distance. In some examples, the distance can be measured using one or more distance metrics, including, but not limited to, an L2 distance, a Manhattan distance, and/or a Cosine distance.

In some embodiments, the step of modifying some or all of the PHI parameters comprises: for each of the PHI parameters: identifying a randomness factor based on clinical relevance data (e.g., as indicated by the modification criteria of clinical relevance data 1106), and selecting, from a distribution of values of a synthetic PHI parameter corresponding to the PHI parameter, a value of the synthetic PHI parameter based on the randomness factor. In one or more examples, the randomness factor of the PHI parameters is inversely proportional to a relevance score associated with each of the PHI parameters. For example, with reference to FIG. 12, clinical relevance data 1106 may include the PHI parameter "Injury" having the clinical relevance score "0.95." Thus, in some examples, the randomness factor for the PHI parameter "Injury" may be "1.05." However, persons of ordinary skill in the art will recognize that the aforementioned is merely illustrative.

Figure 12:
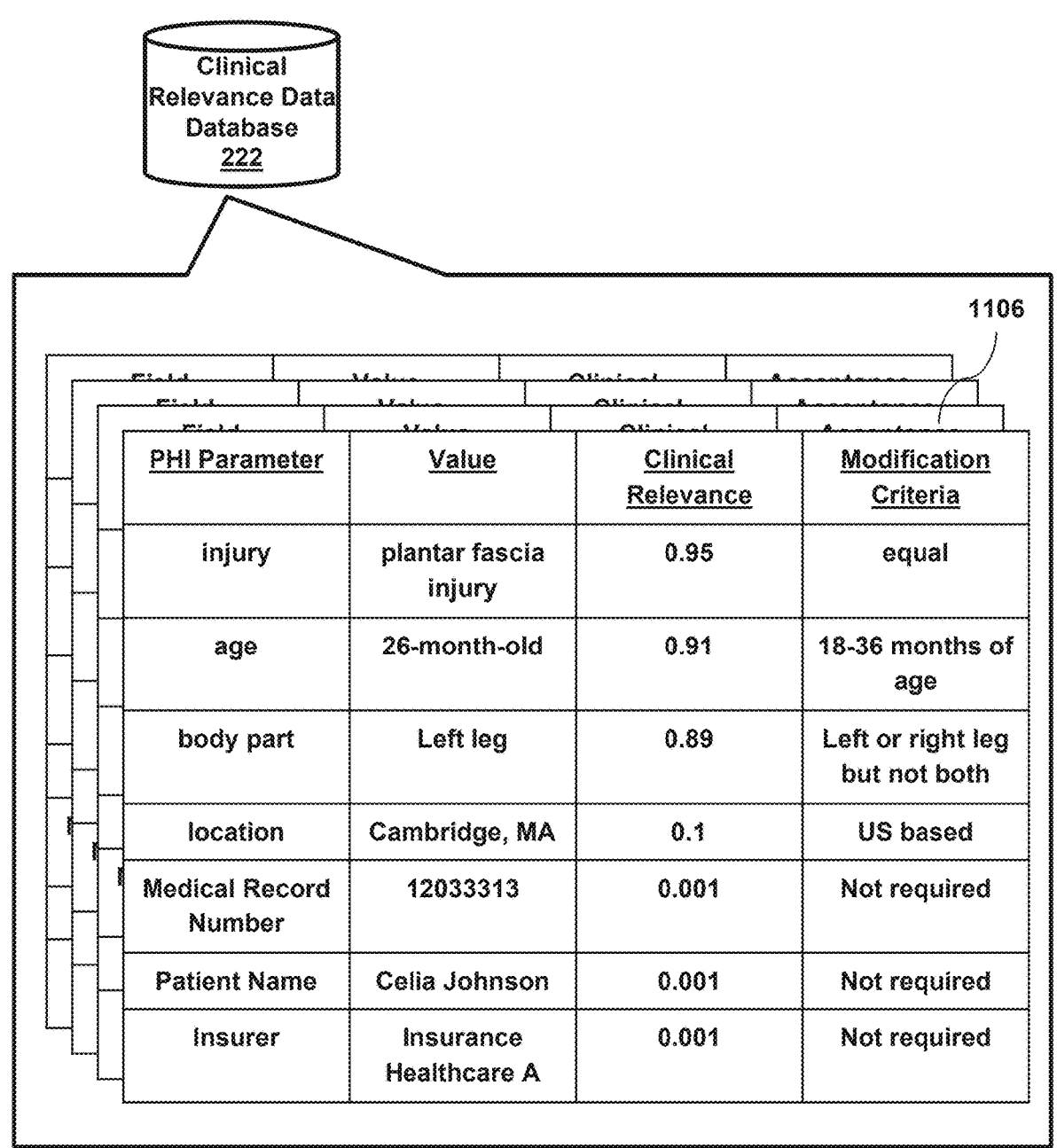
FIG. 12 illustrates an example clinical relevance data database, in accordance with various embodiments.

Clinical relevance data 1106 may describe how relevant a given PHI parameter is to task 410. As seen in FIG. 12, clinical relevance data database 222 may store clinical relevance data associated with a variety of tasks. In one or more examples, the clinical relevance data stored in clinical relevance data database 222 may include clinical relevance data 1106 associated with identified task 410. In some embodiments, clinical relevance data 1106 may include a plurality of data fields corresponding to each of the PHI parameters associated with task 410. In the example of FIG. 12, clinical relevance data 1106 may include populated data fields for the PHI parameters: "injury," "age," "body part," "location," "Medical Record Number," "Patient Name," and "Insurer." For each data field, clinical relevance data 1106 may include a corresponding value derived from user request 204. In some embodiments, the value stored for each data field may comprise a PHI parameter extracted from user request 204. For example, with reference to FIG. 12, clinical relevance data 1106 may indicate that, for task 410, the PHI parameters include "Injury," "Age," "Body Part," "Location," "Medical Record Number," "Patient Name," and "Insurer," having the values "Plantar Fascia Injury," "26-moth-old," "Left leg," "Cambridge, MA," "12033313," "Celia Johnson," and "Insurance Healthcare A," respectively.

Clinical relevance data 1106 may further include clinical relevance values and modification criteria for one or more PHI parameters associated with task 410. For example, different clinical relevance data may be selected for different tasks, and each clinical relevance data may include medical-condition-specific sets of PHI parameters, and the relevancy of those PHI parameters to task 410. In the example of FIG. 12, clinical relevance data 1106 may include the PHI parameters "Injury," "Age," "Body Part," "Location," "Medical Record Number," "Patient Name," and "Insurer." These PHI parameters may have the values: "Plantar Fascia Injury," "26-month-old," "Left leg," "Cambridge, MA," "12033313," "Celia Johnson," and "Insurance A," respectively.

Each PHI parameter may include a clinical relevance score indicating how relevant the value of a corresponding PHI parameter is to the task to be performed by model 220. In one or more examples, the clinical relevance score may be a weight applied to a trained machine learning model when determining what modifications to make to the value of the PHI parameter to obtain a new value of a synthetic version of the PHI parameter. The clinical relevance score may comprise a numerical value between 0 and 1. For example, for the aforementioned PHI parameters and values, the clinical relevance scores may be: "0.95," "0.91," "0.89," "0.1," "0.001," "0.001," and "0.001," respectively.

Each PHI parameter may also include modification criteria indicating which of the values of the corresponding PHI parameters are to be modified and how those values are to be modified. In one or more examples, the modification criteria for the PHI parameters of clinical relevance data 1106, illustrated in FIG. 12, may include "equal," "18-36 months of age," "left leg or right leg but not both," "US based," "Not Required," "Not Required," and "Not Required," respectively associated with PHI parameters: "Injury," "Age," "Body Part," "Location," "Medical Record Number," "Patient Name," and "Insurer." The modification criteria may specify how each value of each PHI parameter can be modified to ensure that revised user request 206 has the same or similar intent as user request 204, and thus causes model 220 to produce response 208 satisfying the requested task.

In some embodiments, process 100 may include a step of generating the one or more synthetic PHI parameters. For example, with respect to FIG. 9, synthetic data generation model 904 may be configured to generate synthetic data based on the values of the data fields stored in data structure 402 and clinical relevance data (e.g., clinical relevance data 1106 shown in FIG. 11 and FIG. 12). In some embodiments, generating the synthetic PHI parameters may comprises: receiving clinical relevance data 1106 based on task 410 and modifying at least some of the PHI parameters based on clinical relevance data 1106 to obtain the synthetic PHI parameters. In some embodiments, synthetic data generation model 904 may be configured to receive, as input, data structure 402, task 410, and clinical relevance data 1106 selected from clinical relevance data database 222, and output synthetic data. In one or more examples, synthetic data generation model 904 may generate one or more synthetic PHI parameters to replace corresponding PHI parameters included in user request 204. In one or more examples, the clinical relevance data (e.g., clinical relevance data 1106) comprises a list of PHI parameters associated with the task and a relevance score associated with each of the PHI parameters. In one or more examples, the clinical relevance data comprises modification criteria associated with each of the data fields. The modification criteria may indicate which of the data fields' values are to be modified and how those values are to be modified.

Figure 13:
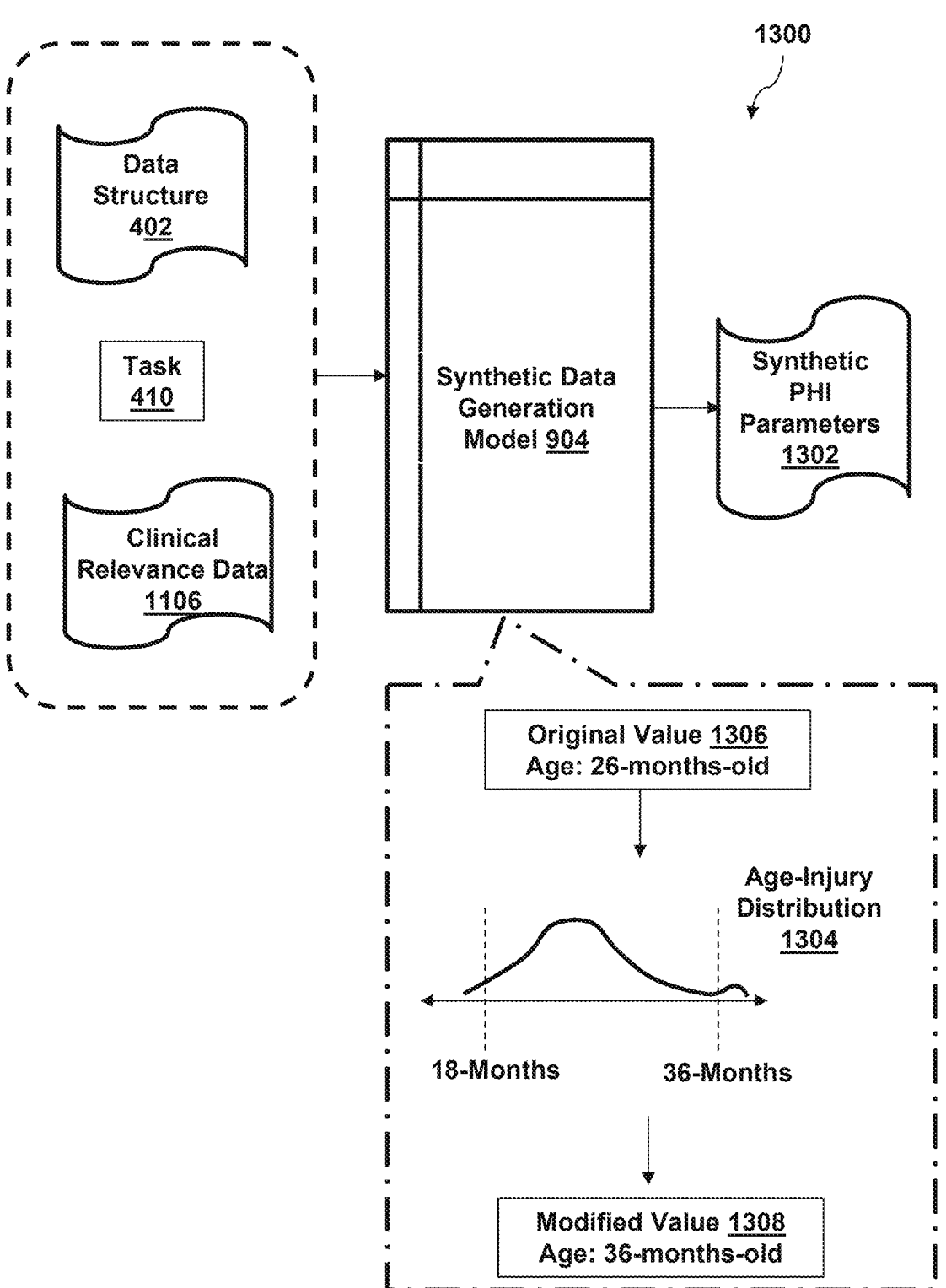
FIG. 13 illustrates an example process for generating synthetic PHI parameters, in accordance with various embodiments.

As an example, with reference to FIG. 13, synthetic data generation process 1300 may include data structure 402, task 410, and clinical relevance data 1106 being input to synthetic data generation model 904. Synthetic data generation model 904 may be trained to output synthetic PHI parameters 1302, whose values comprise the same values or adjusted values of the corresponding PHI parameters from user request 204. As an example, based on the rules included in clinical relevance data 1106, the values generated for synthetic PHI parameters 1302 may include: "Talia Ferber," " ", "Boston, MA," "36-months-old," "plantar fascia injury," "right leg," "Insurance Healthcare B," which respectively correspond to the values "Celia Johnson," "12033313," "Cambridge, MA," "26-months-old," "plantar fascia injury," "left leg," "Insurance Healthcare A" of the PHI parameters from user request 204.

Synthetic data generation model 904 may be trained to adjust a value of a given PHI parameter based on the corresponding clinical relevance score and modification criteria. As an example, with reference again to FIG. 13, user request 204 may indicate that the PHI parameter "Age" has a value 1306: "26-months-old." Synthetic data generation model 904 may determine, based on clinical relevance data 1106, modification criteria associated with the PHI parameter "Age." The modification criteria associated with the PHI parameter "Age" may indicate that for the given value 1306 (e.g., 26-months-old), modified value 1308 can be any value between the range defined by the modification criteria. For example, for value 1306 (e.g., "26-months-old"), modified value 1308 (e.g., "36-months-old") can be randomly selected from an age-injury distribution 1304 between a lower bound of 18-months old and an upper bound of 36-months old. In some cases, the modification criteria may include a weight applied to a value of a selected PHI parameter to change the value to a statistically similar value.

In some embodiments, age-injury distribution 1304 may be generated based on an analysis of electronic health records and health-related statistics. In one or more examples, the health records and statistics are publicly available. In some embodiments, the data can be compiled to determine distributions of values of different PHI parameters. For the example of FIG. 13, age-injury distribution 1304 may be generated by analyzing a number of subjects with a particular injury (e.g., plantar fascia injury) and determining a distribution of the ages of those subjects. Similar distributions can be generated for different PHI parameters. For example, the names of patients with similar injuries or illness can be compiled and a synthetic first name and synthetic surname can be selected for the PHI parameter "Patient Name" can be selected.

In some embodiments, process 100 may include a step of obtaining patient health data associated with a plurality of patients. In one or more examples, the patient health data may include PHI parameters associated with the patients. The patient health data may be retrieved from a plurality of data sources. For example, the patient health data may be accessed from various electronic health record databases.

Furthermore, process 100 may include a step of extracting, using the one or more trained machine learning models, a set of PHI parameters associated with each of the plurality of patients. In some embodiments, a separate data structure may be populated with the extracted PHI parameters for each patient. As an example, the PHI parameters may include "Age," "Condition 1," "Episode," "Condition 2," "Observed," "Latest Lab Result," or other data.

Process 100 may further include a step of generating, using the one or more trained machine learning models, anonymized patient health data by replacing, for each patient, the set of PHI parameters with a corresponding set of synthetic PHI parameters. In some embodiments, the synthesized PHI parameters may be generated using clinical relevance data (e.g., clinical relevance data 1106 of FIG. 11). The anonymized patient health data may now encompass statistically similar information as that of the (non-anonymized) patient health data while also ensuring that a patient's actual personal information and/or health information remains confidential.

In some embodiments, process 100 may include a step of training a non-anonymized machine learning model using the anonymized patient health data, wherein the trained non-anonymized machine learning model is not trained using the set of PHI parameters associated with the plurality of patients. For example, the anonymized training data may be used to train a variety of different models hosted with one or more computing environments (private or public). The trained anonymized machine learning model protects the patient health data of the patients from data leaks. This is particularly useful because the downstream outputs produced by the model are based on the data used to train the model. If the model is trained using actual patient health data, there is a risk that the outputs produced by the model will include traceable patient health information, which compromises the confidentiality measures set in place to protect patients. Additionally, as models can often be a source of security vulnerabilities, such as data leaks and data breaches, using the anonymized patient health data ensures that even if those events occur, the patient's confidential information remains secure.

In some embodiments, process 100 may include a step of determining the relevance score for each of the PHI parameters based on (i) previous user requests comprising the task and (ii) a frequency that the PHI parameter was included in previous responses to the previous user requests. In one or more examples, a plurality of previous user request received by computing system 202 may be accessed. The previous user requests may be accessed from request/response database 228, as shown in FIG. 2. Request/response database 228 may store previously received user requests from various client devices. In some embodiments, each previous user request may include a request identifier that may be stored as metadata associated with the data structure produced for that user request. In some embodiments, similar processes may be performed to the previous user requests as performed to user request 204. For example, PHI parameters may be extracted from the previous user request, a data structure comprising data fields (corresponding to each type of PHI parameter) may be populated with values based on the extracted PHI parameters, a task may be identified based on the data structure, synthetic PHI parameters may be generated based on the data structure and clinical relevance data associated with the task, and a revised previous user request may be generated for the previous user request including the synthetic PHI parameters replacing some or all of the PHI parameters. In some embodiments, request/ response database 228 may store the data structure and revised previous user response generated for each previous user request.

In some embodiments, previous responses generated by model 220 to each of the previous revised user requests may be stored in request/response database 228. In some embodiments, computing system 202 may be configured to determine, for a given task identified for each previous revised user request, a frequency with which a particular PHI parameter (or synthetic PHI parameter) was included in the previous response to that previous revised user request. Thus, computing system 202 can build relevance scores for each of the PHI parameters based on how frequently those PHI parameters were included in previous responses generated by model 220. As an example, as illustrated by FIG. 12, certain PHI parameters have a higher clinical relevance score than others, indicating that those PHI parameters are more important to a response generated by model 220 than PHI parameters having a lower clinical relevance score.

In some embodiments, process 100 may include a step of generating a mapping between the PHI parameters from user request 204 and the synthetic PHI parameters used in revised user request 206. Mapping 908 can be used downstream for constructing a revised response (e.g., revised response 226 of FIG. 2) from model 220 including the original PHI parameters from user request 204. As an example, with reference to FIG. 9, parameter mapping module 906 may be configured to generate a mapping 908 indicating a relationship between the values of each of the PHI parameters extracted from user request 204 and the modified values of each of the synthetic PHI parameters generated based on a corresponding value of that PHI parameter, task 410, and clinical relevance data 1106. An example mapping database 214 storing mapping 908 is illustrated in FIG. 14.

In some embodiments, mapping 908 may comprise a data structure populated with private information associated with the patient. For example, mapping 908 may include the PHI parameter "Body Part," and having the value "Left Leg." The synthetic data generation process may modify the value of this data field to be "Right Leg," based at least in part on the modification criteria stored in clinical relevance data 1106. Thus, mapping 908 stores the relationships between the PHI parameters and the synthetic PHI parameters, which allows computing system 202 to replace the synthetic PHI parameters with the original PHI parameters during formation of revised response 226. In some embodiments, mapping 908 may store the synthetic PHI parameters. In one or more examples, the values stored in each PHI parameter's data field can represent the extracted PHI parameter and the synthesized PHI parameter which comprises an anonymized version of the private information of the extracted PHI parameter. For example, mapping 908 may store that for the PHI parameter "Patient Name," a data field may store the value "Celia Johnson" as being associated with the extracted PHI parameter and the value "Talia Ferber" as being associated with the synthetic PHI parameter:

{'T': 'Patient Name', 'E': 'Celia Johnson'}

{'T': 'Synthetic Patient Name', 'E': 'Talia Ferber'}.

As seen from the example above, the data field for the PHI parameter "Patient Name" is populated with the value "Celia Johnson," and this field-value tuple may be mapped to the field-value tuple {"Synthetic Patent Name": "Talia Ferber"}. Thus, the value populating the data field of the synthetic PHI parameter: {"Patient Name": "Talia Ferber" } may be used to replace the value populating the data field of the PHI parameter: {"Patient Name": "Celia Johnson" } in revised user request 206. This can ensure that the confidential and private patient data, such as the patient's actual name, is not included in the user request provided to model 220 operating in a public (or more generally, non-private), computing environment.

Figure 15:
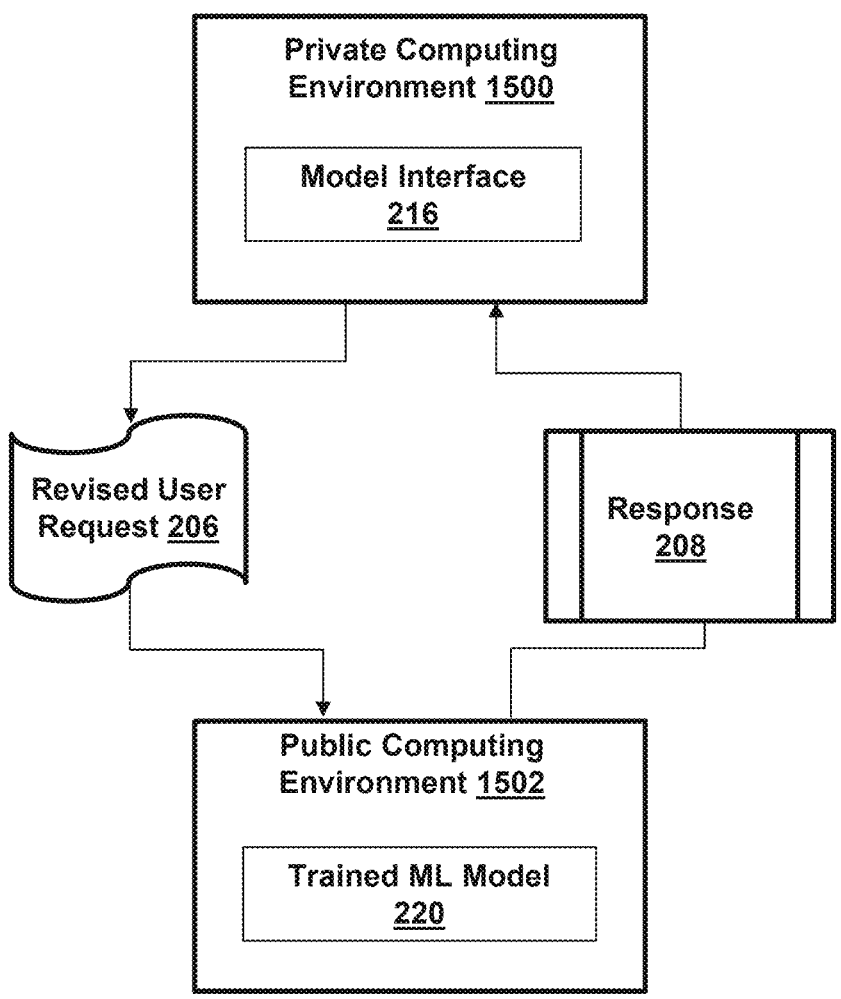
FIG. 15 illustrates an example session between a private computing environment and a public computing environment, in accordance with various embodiments.

Returning to step 108 of FIG. 1, the revised user request may be provided to a trained external machine learning model. For example, with reference to FIG. 2, revised user request 206 may be input to model 220, which may generate response 208. In some embodiments, model 220 comprise a large language model (LLM). In one or more examples, as seen with reference to FIG. 15, the trained machine learning models of computing system 202 may be deployed on a private computing environment 1500 and model 220 may be deployed on a public computing environment 1502. In some embodiments, revised user request 206 may be input to model 220 via an application programming interface (API) prompt. For example, private computing environment 1500 may include model interface 216 of computing system 202. Model interface 216 may facilitate revised user request 206 being provided to model 220 and receiving response 208 therefrom.

In some embodiments, model interface 216 may include logic to encrypt revised user request 206, as well as data transmitted with revised user request 206. For example, a data structure of synthetic PHI parameters associated with revised user request 206 may be input to model 220. The synthetic PHI parameters, as well as revised user request 206, may be encrypted using one or more encryption techniques (e.g., RSA).

Returning to step 110 of FIG. 1, a response to the task may be received from the trained external machine learning model, where the response comprises the one or more synthetic PHI parameters. For example, as seen with reference to FIG. 2, response 208 may be received by computing system 202 from model 220.

In some embodiments, a structure of the response is determined based on the task. As an example, with reference to FIG. 16, response 208 may be structured as a letter. The structure of response 208 may be selected by model 220 based on task 410 determined for user request 204 (and subsequently revised user request 206). For example, based on the identified task (e.g., task 410) of user request 204, model 220 may generate a letter. As another example, for a different task, a different response structure may be selected. In some embodiments, the particular structure of response 208 may depend on the identified task. As an example, medical referral requests, protected health information update requests, or other types of requests may generally result in letter-like responses being produced by model 220. As another example, financial requests or education requests may result in model 220 producing a spreadsheet, plot, or other structure. As seen in FIG. 16, response 208 may include synthetic PHI parameters—represented by the underlined text. The synthetic PHI parameters may, as described above, be generated based on the PHI parameters extracted from user request 204, the identified task (e.g., task 410), clinical relevance data associated with the identified task (e.g., clinical relevance data 1106), or other information.

Returning to FIG. 1, at step 112, a revised response to the task may be generated using the trained machine learning models by replacing the one or more synthetic PHI parameters with the one or more PHI parameters. In some embodiments, response revision subsystem 218 may be configured to generate revised response 226 based on response 208 and mapping 908 (described above with reference to FIG. 9). Response revision subsystem 218 may implement a synthetic PHI parameter identification model 1702 and may include a parameter re-mapping module 1704, as well as other components.

Figure 17:
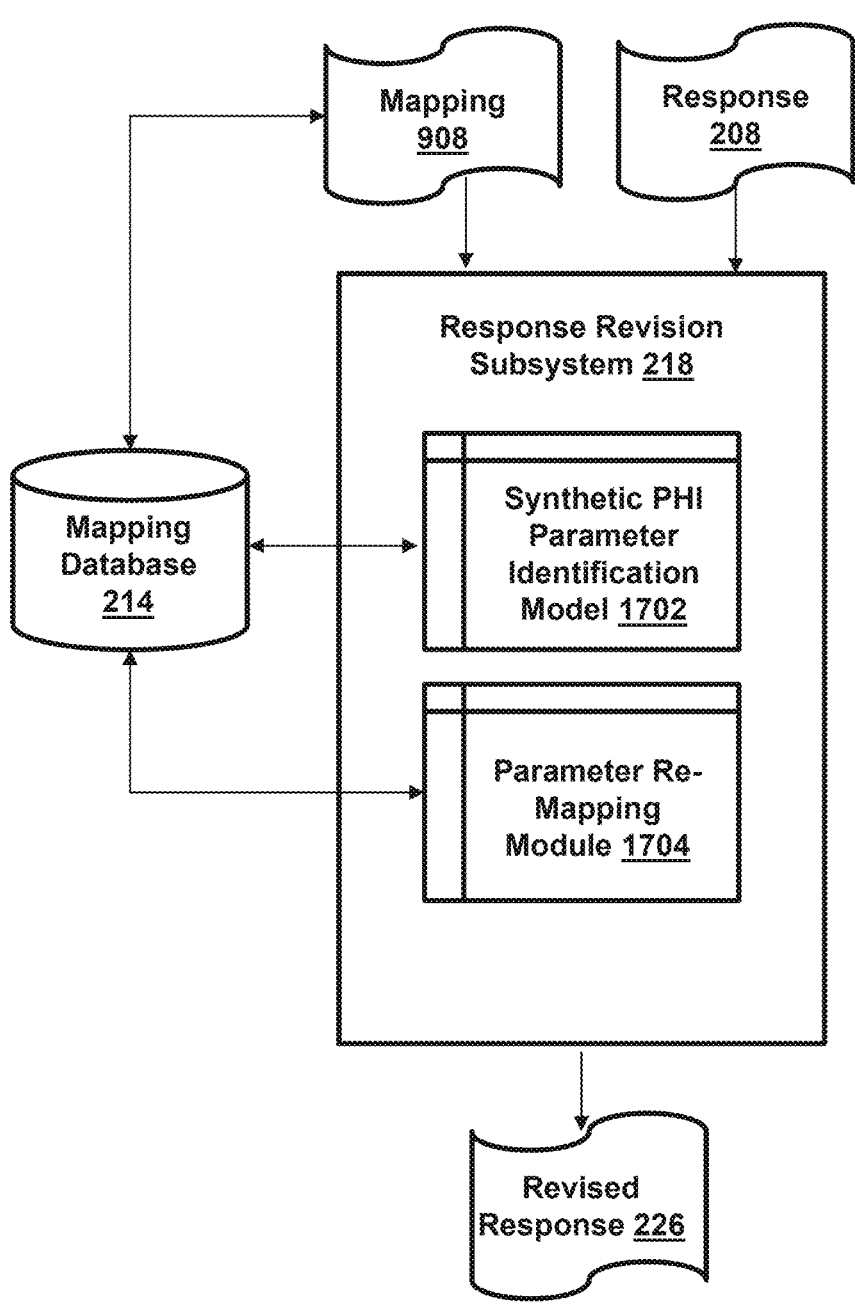
FIG. 17 illustrates an example response revision subsystem, in accordance with various embodiments.

With reference to FIG. 17, synthetic PHI parameter identification model 1702 may be configured to implement one or more models for identifying synthetic PHI parameters within response 208. In one or more examples, synthetic PHI parameter model 1702 may identify the synthetic PHI parameters in response 208 based on mapping 908. For example, mapping 908 may include a list of all of the synthetic PHI parameters. Synthetic PHI parameter identification model 1702 may scan response 208 to determine whether response 208 includes one or more instances of any of the synthetic PHI parameters. In some embodiments, synthetic PHI parameter identification model 1702 may implement one or more NLP models and/or one or more computer vision models. For example, synthetic PHI parameter identification model 1702 may implement one or more NLP models that are the same or similar to NLP models 404, one or more computer vision models that are the same or similar to computer vision models 406, or combinations thereof. In one or more examples, the NLP models implemented by synthetic PHI parameter identification model 1702 may be trained to tokenize text within response 208, perform entity recognition and entity resolution, natural language understanding, or other language processing steps. In one or more examples, synthetic PHI parameter identification model 1702 may be trained to recognize text or phrases within response 208. For example, synthetic PHI parameter identification model 1702 may compute a similarity for each synthetic PHI parameter value and determine whether any text from response 208 matches (e.g., has a similarity score greater than or equal to a text similarity threshold score) the synthetic PHI parameter. If so, then synthetic PHI parameter identification model 1702 may flag that text as representing an instance of a synthetic PHI parameter within response 208.

In some embodiments, generating the revised response at step 112 may comprises accessing the mapping to determine which of the PHI parameters are to replace each of the synthetic PHI parameters. For example, parameter re-mapping module 1704 may be configured to determine, based on mapping 908, which synthetic PHI parameters from response 208 are to be replaced with the PHI parameters extracted from user request 204. In some embodiments, parameter re-mapping module 1704 may determine, for each synthetic PHI parameter value, a corresponding value of the PHI parameter extracted from user request 204. As an example, with reference again to FIG. 16, parameter re-mapping module 1704 may determine that response 208 includes text and at least some of the text matches one or more synthetic PHI parameters, such as the synthetic patient name "Talia Ferber." Using mapping 908 and response 208, parameter re-mapping module 1704 may be configured to replace the synthetic PHI parameter values with their corresponding PHI parameter values. As an example, with reference to FIG. 18, revised response 226 may include the PHI parameter "Patient Name" having a value "Celia Johnson."

In some embodiments, process 100 may further include a step of determining whether the user request is part of an existing session between a client device and the trained external machine learning model. For example, when a client device submits an initial user request, model 220 may create a session log. The session log may include references (e.g., pointers to the input user request and output response, timestamps, etc.) to each request input to model 220 and each response output by model 220. In some embodiments, an identifier for the existing session may be generated for the initial user request, and each subsequent communication between the client device and model 220 may include metadata indicating the identifier.

In some embodiments, process 100 may further include a step of appending a history of the existing session to include the user request (e.g., user request 204, revised user request 206, or other user requests) based on the user request being determined to be part of the existing session. For example, if the user request is part of an existing session between the client device and the trained external machine learning model, then the received user request, as well as the revised user request, may be added to the existing session's history. In some embodiments, a user request may be identified as being part of an existing session based on a time that the user request was received by model 220 and a time that the initial user request was received by model 220 and/or a time that most recent user request/response was received/output by model 220. For example, if the amount of time between when the user request was received and when a most recent response was output by model 220 is less than a threshold amount of time (e.g., less than 30 seconds, less than 10 seconds, less than 5 seconds, less than 1 second, etc.), then the user request may be classified as being part of the existing session.

In some embodiments, process 100 may further include a step of creating a new session between the client device and the trained external machine learning model. For example, if model 220 determines that the time between the user request being input to model 220 and the most recent response output by model 220 is greater than or equal to the threshold amount of time, then this may indicate that the user request is part of a new session. In one or more examples, the new session may include the user request. In some embodiments, process 100 may further include a step of adding the response to the task and the revised response to the task to a history of the new session.

Figure 19:
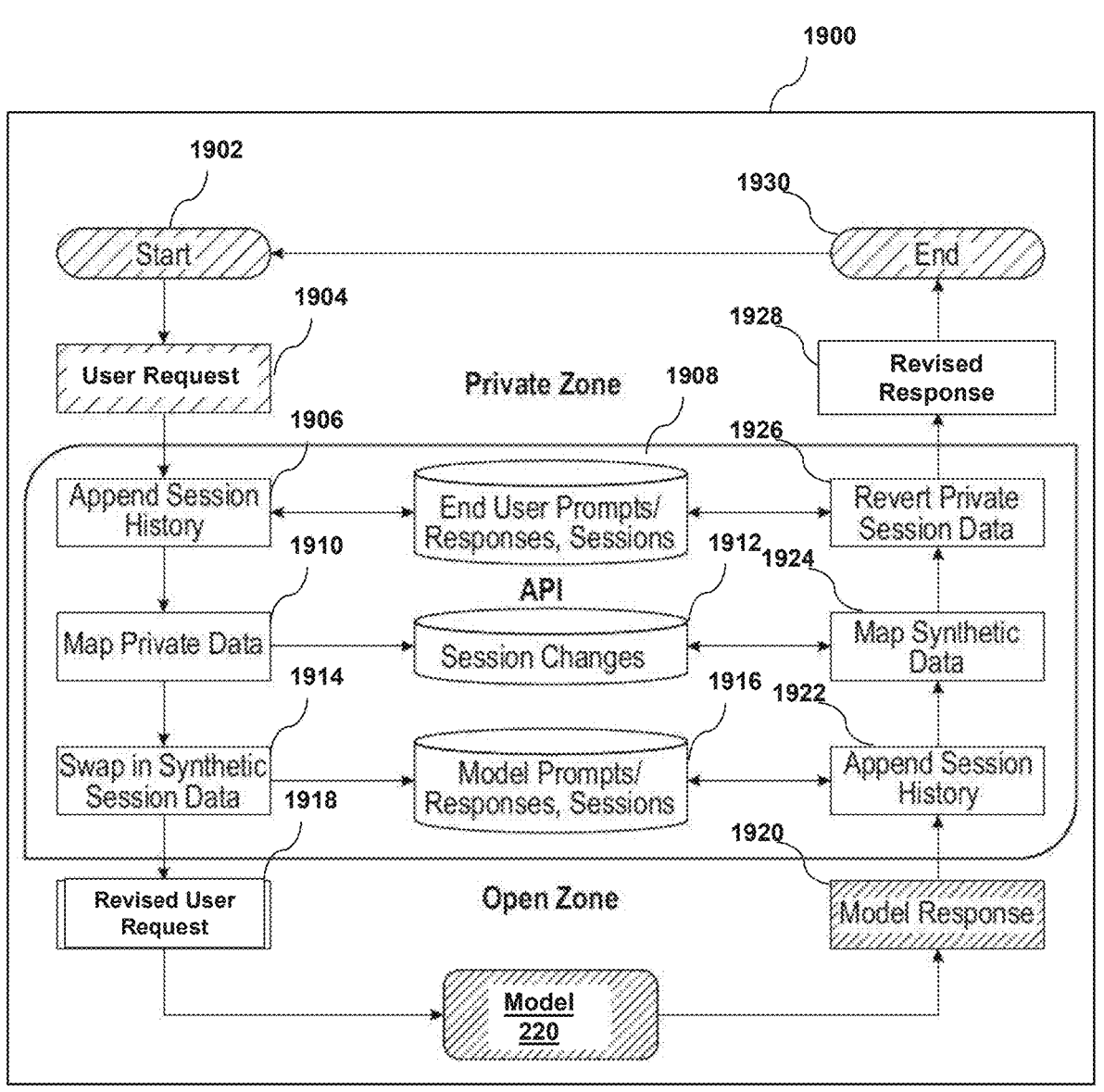
FIG. 19 illustrates an example session creation/modification process, in accordance with various embodiments.

As an example, with reference to FIG. 19, process 1900 may start at 1902 where a user request 1904 may be received. In some examples, user request 1904 may be the same or similar to user request 204 described above. Model interface 216 may be configured to receive user request 1904 at 1906. In some examples, at 1906, database 1908 may be queried to determine whether user request 1904 includes prompts indicating that an existing session between a client device and model 220 is continuing or a new session is starting. If an existing session exists, then at 1906, the session history for the existing session may be appended based on user request 1904. If not, at 1906, a new session log may be generated and stored in database 1908. At 1910, the private data may be mapped to the synthetic data (e.g., via mapping 908), and any changes to the terms included in the user requests across the session may be stored in database 1912. For example, if the PHI parameter "Location" is updated from a first value (e.g., "Cambridge, MA") from a first user request in a session to a second value (e.g., "Boston, MA") from a second user request, the updates may be stored in database 1912. At 1914, the synthetic PHI parameters may be replaced at the prescribed location within user request 1904 to output revised user request 1918. In some embodiments, the swapped parameters may be stored in database 1916. Database 1916 may be linked to database

1908 and may share data. For example, database 1908 may store session information associated with any submitted user requests and database 1916 may store session information associated with any response generated by model 220. In some examples, revised user request 1918 may be the same or similar to revised user request 206 described above. Revised user request 1918 may be input to model 220 operating in a public and open computing environment. As an example, model 220 may include one or more third party models.

In some embodiments, third party models 220 may output a response 1920. Response 1920 may include the synthetic PHI parameters that were replaced in revised user request 1918 at 1914. In one or more examples, response 1920 may be the same or similar to response 208 described above. After receiving response 1920, at 1922, model interface 216 may be configured to append the session history to include response 1920. For example, the session history stored in database 1908 and 1916 may be appended to link response data from response 1920 to user request 1904. At 1924, the mapping generated and stored in 1912 may be accessed to relate the synthetic PHI parameters included in response 1920 with the PHI parameters included in user request 1904. At 1926, the synthetic PHI parameters may be replaced with the PHI parameters from user request 1904 based on the mapping (e.g., mapping 908). Model interface 216 may be configured to output revised response 1928, which may be the same or similar to revised response 226. After determining that no additional inputs/prompts have been received, process 1900 may end at 1930.

It should be noted that while one or more operations are described herein as being performed by particular components of computing system 202, those operations may, in some embodiments, be performed by other components of computing system 202 or other components of system 200. As an example, while one or more operations are described herein as being performed by components of computing system 202, those operations may, in some embodiments, be performed by aspects of one or more client devices. It should also be noted that, although some embodiments are described herein with respect to machine learning models, other prediction models (e.g., statistical models or other analytics models) may be used in lieu of or in addition to machine learning models (e.g., a statistical model replacing a machine-learning model and a non-statistical model replacing a non-machine-learning model in one or more embodiments). Still further, although a single instance of computing system 202 is depicted within FIG. 2, additional instances of computing system 202 may be included (e.g., computing system 202 may comprise a distributed computing system).

Although not illustrated, other intermediary devices (e.g., data stores of a server connected to computing system 202) can also be used. The components of system 200 of FIG. 2 can be used in a variety of applications where de-identifying and anonymizing data are essential components of the work. For example, such applications may include leveraging trained external machine learning models, such as LLMs, which tend to operate within public computing environments. By de-identifying and anonymizing the data, private information may be kept confidential to the trained external machine learning models and other entities capable of accessing the public computing environments. Some example applications include, but are not limited to, protected health information, educational information, legal information, financial information, criminal information, etc.

The machine learning techniques that can be used in the systems/subsystems/modules described herein may include, but are not limited to (which is not to suggest that any other list is limiting), any of the following: Ordinary Least Squares Regression (OLSR), Linear Regression, Logistic Regression, Stepwise Regression, Multivariate Adaptive Regression Splines (MARS), Locally Estimated Scatterplot Smoothing (LOESS), Instance-based Algorithms, k-Nearest Neighbor (KNN), Learning Vector Quantization (LVQ), Self-Organizing Map (SOM), Locally Weighted Learning (LWL), Regularization Algorithms, Ridge Regression, Least Absolute Shrinkage and Selection Operator (LASSO), Elastic Net, Least-Angle Regression (LARS), Decision Tree Algorithms, Classification and Regression Tree (CART), Iterative Dichotomizer 3 (ID3), C4.5 and C5.0 (different versions of a powerful approach), Chi-squared Automatic Interaction Detection (CHAID), Decision Stump, M5, Conditional Decision Trees, Naive Bayes, Gaussian Naive Bayes, Causality Networks (CN), Multinomial Naive Bayes, Averaged One-Dependence Estimators (AODE), Bayesian Belief Network (BBN), Bayesian Network (BN), k-Means, k-Medians, K-cluster, Expectation Maximization (EM), Hierarchical Clustering, Association Rule Learning Algorithms, A-priori algorithm, Eclat algorithm, Artificial Neural Network Algorithms, Perceptron, Back-Propagation, Hopfield Network, Radial Basis Function Network (RBFN), Deep Learning Algorithms, Deep Boltzmann Machine (DBM), Deep Belief Networks (DBN), Convolutional Neural Network (CNN), Deep Metric Learning, Stacked Auto-Encoders, Dimensionality Reduction Algorithms, Principal Component Analysis (PCA), Principal Component Regression (PCR), Partial Least Squares Regression (PLSR), Collaborative Filtering (CF), Latent Affinity Matching (LAM), Cerebri Value Computation (CVC), Multidimensional Scaling (MDS), Projection Pursuit, Linear Discriminant Analysis (LDA), Mixture Discriminant Analysis (MDA), Quadratic Discriminant Analysis (QDA), Flexible Discriminant Analysis (FDA), Ensemble Algorithms, Boosting, Bootstrapped Aggregation (Bagging), AdaBoost, Stacked Generalization (blending), Gradient Boosting Machines (GBM), Gradient Boosted Regression Trees (GBRT), Random Forest, Computational intelligence (evolutionary algorithms, etc.), Computer Vision (CV), Natural Language Processing (NLP), Recommender Systems, Reinforcement Learning, Graphical Models, or separable convolutions (e.g., depth-separable convolutions, spatial separable convolutions).

Figure 20:
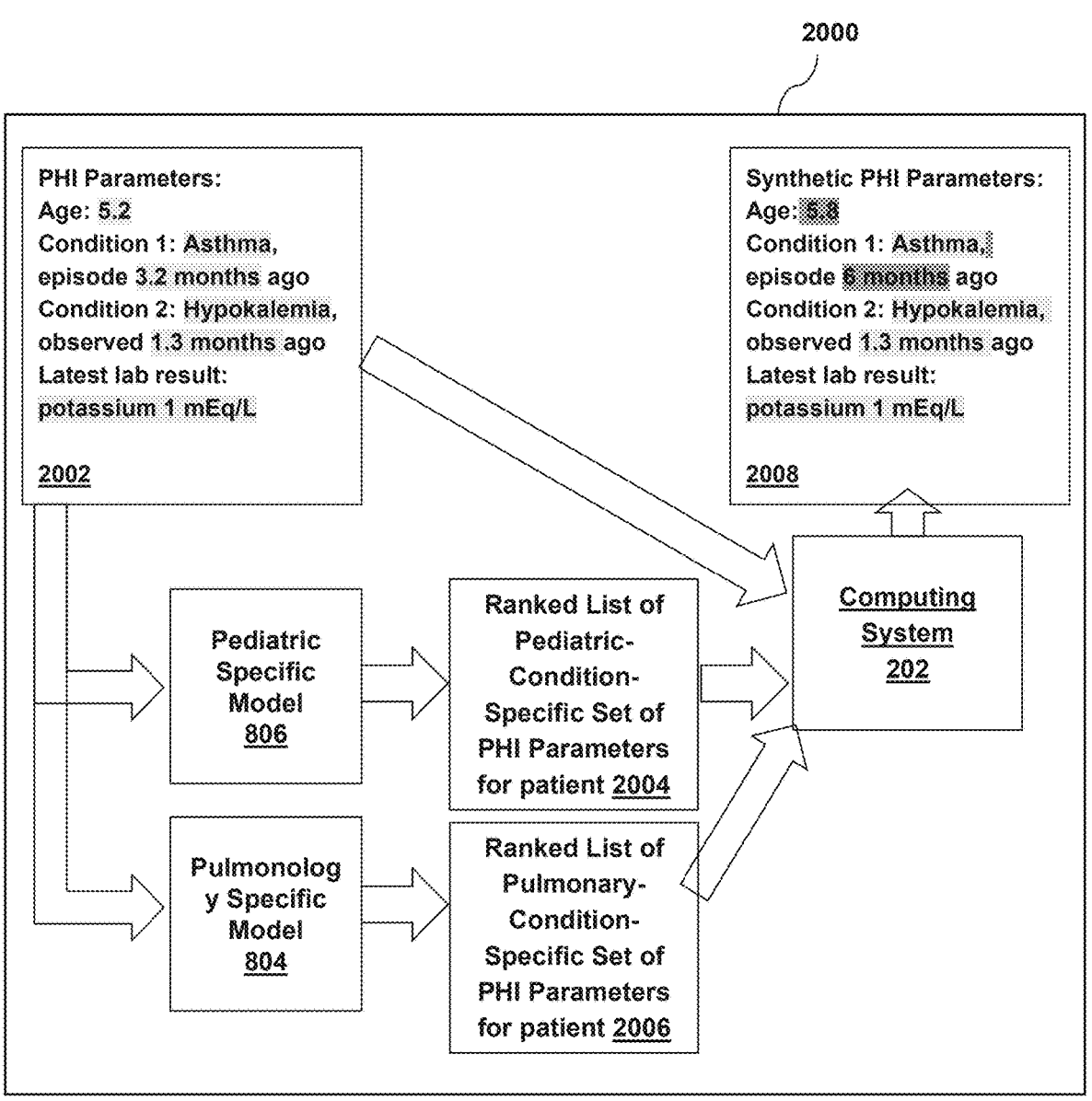
FIG. 20 illustrates an example process for generating synthetic PHI parameters, in accordance with various embodiments.

As an illustrative example, FIG. 20 depicts a process 2000 of generating synthetic PHI parameters 2008 based on PHI parameters 2002 extracted from a user request. As an example, PHI parameters 2002 may include "Age," "Condition 1," "Episode," "Condition 2," "Observed," "Latest Lab Result," or other data. In some embodiments, computing system 202 may determine one or more trained machine learning models to retrieve from model database 224 to generate synthetic PHI parameters 2008. In the example of FIG. 20, based on the PHI parameter "Age," and "Condition 1," having the values "5.2" and "Asthma," computing system 202, and in particular task identification model 408, may determine that the user request including PHI parameters 2002 relates to a pediatric patient with a pulmonary illness. Thus, computing system 202 may be configured to retrieve pediatric-specific model 806 and pulmonology-specific model 804, which can be used to analyze the user request including PHI parameters 2002 and generate synthetic PHI parameters 2008.

In some embodiments, each medical-condition-specific model may include a medical-condition-specific set of PHI parameters. In some embodiments, the medical-condition-specific models may rank a relevancy of each of the medical-condition-specific set of PHI parameters based on the identified task of the user request and the extracted PHI parameters 2002. For example, the PHI parameters most relevant to a pediatric-specific task may be ranked based on the patient represented by PHI parameters 2002, as indicated by ranking 2004. As another example, the PHI parameters most relevant to a pulmonary-specific task may be ranked based on the patient represented by PHI parameters 2002, as indicated by ranking 2006. In some embodiments, ranking 2004 and ranking 2006 may be provided to computing system 202 for generating synthetic PHI parameters 2008.

Figure 21:
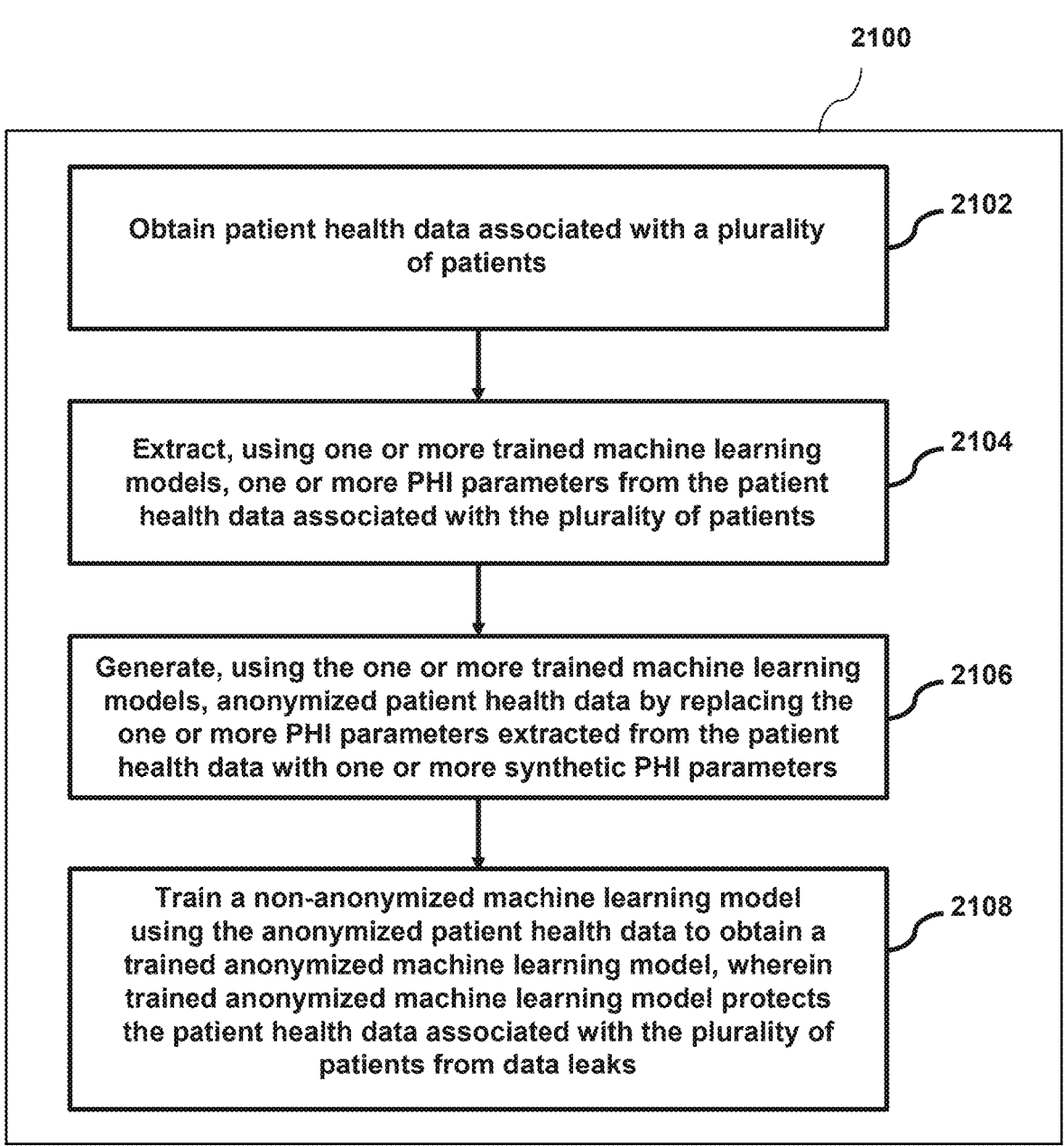
FIG. 21 illustrates an example method for training a non-anonymized machine learning model, in accordance with various embodiments.

FIG. 21 illustrates an example method 2100 for training a non-anonymized machine learning model, in accordance with various embodiments. Method 2100 may begin, for example, at step 2102. At step 2102, patient health data associated with a plurality of patients may be obtained. The patient health data may include PHI parameters associated with the patients. The patient health data may be retrieved from a plurality of data sources. For example, the patient health data may be accessed from various electronic health record databases.

At step 2104, one or more trained machine learning models may be used to extract one or more PHI parameters from the patient health data associated with the patients. In some embodiments, a separate data structure may be populated with the extracted PHI parameters for each patient. As an example, the PHI parameters may include "Age," "Condition 1," "Episode," "Condition 2," "Observed," "Latest Lab Result," or other data.

At step 2106, the trained machine learning models may be used to generate anonymized patient health data by replacing the extracted PHI parameters extracted from the patient health data with one or more synthesized PHI parameters. In some embodiments, the synthesized PHI parameters may be generated using clinical relevance data (e.g., clinical relevance data 1106 of FIG. 11). The anonymized patient health data may now encompass statistically similar information as that of the (non-anonymized) patient health data while also ensuring that a patient's actual personal information and/or health information remains confidential.

At step 2108, a non-anonymized machine learning model may be trained using the anonymized patient health data to obtain a trained anonymized machine learning model. The trained anonymized machine learning model protects the patient health data of the patients from data leaks. This is particularly useful because the downstream outputs produced by the model are based on the data used to train the model. If the model is trained using actual patient health data, there is a risk that the outputs produced by the model will include traceable patient health information, which compromises the confidentiality measures set in place to protect patients. Additionally, as models can often be a source of security vulnerabilities, such as data leaks and data breaches, using the anonymized patient health data ensures that even if those events occur, the patient's confidential information remains secure.

Method 2100 may be used in a variety of different contexts. For example, method 2100 may be used to generate anonymized patient health data that can be then used during a fine-tuning training stage for a pre-trained model and/or transfer learning. As another example, the generated anonymized patient health data may be used at the initial training stage. As yet another example, the generated anonymized patient health data may be used in reinforcement learning, where machine and/or man-in the middle actors could be used to train the model while also protecting the patient health data from unsolicited exposure.

Figure 22:
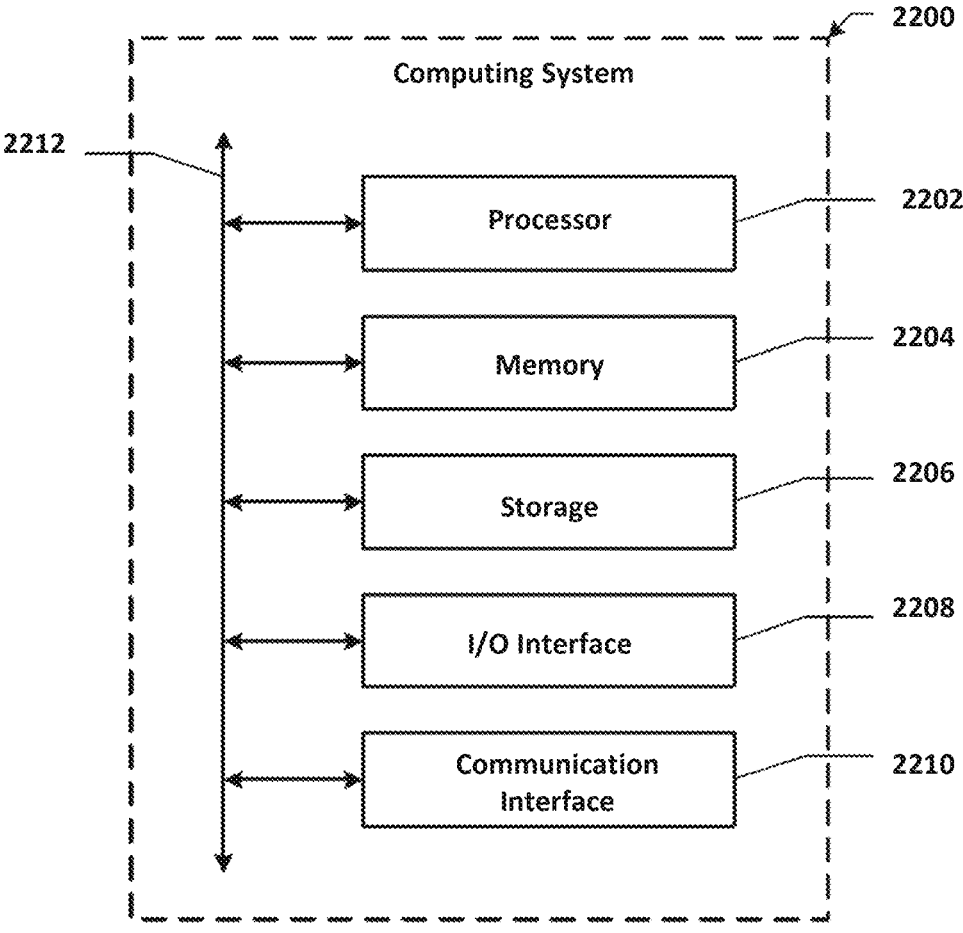
FIG. 22 illustrates an example computer system used to implement some or all of the techniques described herein.

FIG. 22 illustrates an example computer system 2200. In some embodiments, one or more computer systems 2200 perform one or more steps of one or more methods described or illustrated herein. In some embodiments, one or more computer systems 2200 provide functionality described or illustrated herein. In some embodiments, software running on one or more computer systems 2200 performs one or more steps of one or more methods described or illustrated herein or provides functionality described or illustrated herein. Particular embodiments include one or more portions of one or more computer systems 2200. Herein, reference to a computer system may encompass a computing device, and vice versa, where appropriate. Moreover, reference to a computer system may encompass one or more computer systems, where appropriate.

This disclosure contemplates any suitable number of computer systems 2200. This disclosure contemplates computer system 2200 taking any suitable physical form. As example and not by way of limitation, computer system 2200 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, or a combination of two or more of these. Where appropriate, computer system 2200 may include one or more computer systems 2200; be unitary or distributed; span multiple locations; span multiple machines; span multiple data centers; or reside in a cloud, which may include one or more cloud components in one or more networks. Where appropriate, one or more computer systems 2200 may perform without substantial spatial or temporal limitation one or more steps of one or more methods described or illustrated herein. As an example, and not by way of limitation, one or more computer systems 2200 may perform in real time or in batch mode one or more steps of one or more methods described or illustrated herein. One or more computer systems 2200 may perform at various times or at different locations one or more steps of one or more methods described or illustrated herein, where appropriate.

In some embodiments, computer system 2200 includes a processor 2202, memory 2204, storage 2206, an input/output (I/O) interface 2208, a communication interface 2210, and a bus 2212. Although this disclosure describes and illustrates a particular computer system having a particular number of components in a particular arrangement, this disclosure contemplates any suitable computer system having any suitable number of any suitable components in any suitable arrangement.

In some embodiments, processor 2202 includes hardware for executing instructions, such as those making up a computer program. As an example, and not by way of limitation, to execute instructions, processor 2202 may retrieve (or fetch) the instructions from an internal register, an internal cache, memory 2204, or storage 2206; decode and execute them; and then write one or more results to an internal register, an internal cache, memory 2204, or storage 2206. In some embodiments, processor 2202 may include one or more internal caches for data, instructions, or addresses. This disclosure contemplates processor 2202 including any suitable number of any suitable internal caches, where appropriate. As an example, and not by way of limitation, processor 2202 may include one or more instruction caches, one or more data caches, and one or more translation lookaside buffers (TLBs). Instructions in the instruction caches may be copies of instructions in memory 2204 or storage 2206, and the instruction caches may speed up retrieval of those instructions by processor 2202. Data in the data caches may be copies of data in memory 2204 or storage 2206 for instructions executing at processor 2202 to operate on; the results of previous instructions executed at processor 2202 for access by subsequent instructions executing at processor 2202 or for writing to memory 2204 or storage 2206; or other suitable data. The data caches may speed up read or write operations by processor 2202. The TLBs may speed up virtual-address translation for processor 2202. In some embodiments, processor 2202 may include one or more internal registers for data, instructions, or addresses. This disclosure contemplates processor 2202 including any suitable number of any suitable internal registers, where appropriate. Where appropriate, processor 2202 may include one or more arithmetic logic units (ALUs); be a multi-core processor; or include one or more processors 2202. Although this disclosure describes and illustrates a particular processor, this disclosure contemplates any suitable processor.

In some embodiments, memory 2204 includes main memory for storing instructions for processor 2202 to execute or data for processor 2202 to operate on. As an example, and not by way of limitation, computer system 2200 may load instructions from storage 2206 or another source (such as, for example, another computer system 2200) to memory 2204. Processor 2202 may then load the instructions from memory 2204 to an internal register or internal cache. To execute the instructions, processor 2202 may retrieve the instructions from the internal register or internal cache and decode them. During or after execution of the instructions, processor 2202 may write one or more results (which may be intermediate or final) to the internal register or internal cache. Processor 2202 may then write one or more of those results to memory 2204. In some embodiments, processor 2202 executes only instructions in one or more internal registers or internal caches or in memory 2204 (as opposed to storage 2206 or elsewhere) and operates only on data in one or more internal registers or internal caches or in memory 2204 (as opposed to storage 2206 or elsewhere). One or more memory buses (which may each include an address bus and a data bus) may couple processor 2202 to memory 2204. Bus 2212 may include one or more memory buses, as described below. In some embodiments, one or more memory management units (MMUs) reside between processor 2202 and memory 2204 and facilitate access to memory 2204 requested by processor 2202. In some embodiments, memory 2204 includes random access memory (RAM). This RAM may be volatile memory, where appropriate. Where appropriate, this RAM may be dynamic RAM (DRAM) or static RAM (SRAM). Moreover, where appropriate, this RAM may be single-ported or multi-ported RAM. This disclosure contemplates any suitable RAM. Memory 2204 may include one or more memories 2204, where appropriate. Although this disclosure describes and illustrates particular memory, this disclosure contemplates any suitable memory.

In some embodiments, storage 2206 includes mass storage for data or instructions. As an example, and not by way of limitation, storage 2206 may include a hard disk drive (HDD), a floppy disk drive, flash memory, an optical disc, a magneto-optical disc, magnetic tape, or a Universal Serial Bus (USB) drive or a combination of two or more of these. Storage 2206 may include removable or non-removable (or fixed) media, where appropriate. Storage 2206 may be internal or external to computer system 2200, where appropriate. In some embodiments, storage 2206 is non-volatile, solid-state memory. In some embodiments, storage 2206 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 2206 taking any suitable physical form. Storage 2206 may include one or more storage control units facilitating communication between processor 2202 and storage 2206, where appropriate. Where appropriate, storage 2206 may include one or more storages 2206. Although this disclosure describes and illustrates particular storage, this disclosure contemplates any suitable storage.

In some embodiments, I/O interface 2208 includes hardware, software, or both, providing one or more interfaces for communication between computer system 2200 and one or more I/O devices. Computer system 2200 may include one or more of these I/O devices, where appropriate. One or more of these I/O devices may enable communication between a person and computer system 2200. As an example, and not by way of limitation, an I/O device may include a keyboard, keypad, microphone, monitor, mouse, printer, scanner, speaker, still camera, stylus, tablet, touch screen, trackball, video camera, another suitable I/O device, or a combination of two or more of these. An I/O device may include one or more sensors. This disclosure contemplates any suitable I/O devices and any suitable I/O interfaces 2208 for them. Where appropriate, I/O interface 2208 may include one or more device or software drivers enabling processor 2202 to drive one or more of these I/O devices. I/O interface 2208 may include one or more I/O interfaces 2208, where appropriate. Although this disclosure describes and illustrates a particular I/O interface, this disclosure contemplates any suitable I/O interface.

In some embodiments, communication interface 2210 includes hardware, software, or both providing one or more interfaces for communication (such as, for example, packet-based communication) between computer system 2200 and one or more other computer systems 2200 or one or more networks. As an example, and not by way of limitation, communication interface 2210 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 2210 for it. As an example, and not by way of limitation, computer system 2200 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 2200 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 2200 may include any suitable communication interface 2210 for any of these networks, where appropriate. Communication interface 2210 may include one or more communication interfaces 2210, where appropriate. Although this disclosure describes and illustrates a particular communication interface, this disclosure contemplates any suitable communication interface.

In some embodiments, bus 2212 includes hardware, software, or both coupling components of computer system 2200 to each other. As an example and not by way of limitation, bus 2212 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 2212 may include one or more buses 2212, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. Additionally, although this disclosure describes or illustrates particular embodiments as providing particular advantages, particular embodiments may provide none, some, or all of these advantages.

EXAMPLE EMBODIMENTS

Embodiments disclosed herein may include:

1. A method for performing a task using a trained external machine learning model, comprising: receiving a user request comprising the task and one or more protected health information (PHI) parameters associated with a patient; extracting, using one or more trained machine learning models, the one or more PHI parameters associated with the patient; generating, using the one or more trained machine learning models, a revised user request by replacing the one or more PHI parameters in the user request with one or more synthetic PHI parameters; providing the revised user request to the trained external machine learning model; receiving, from the trained external machine learning model, a response to the task comprising the one or more synthetic PHI parameters; and generating, using the one or more trained machine learning models, a revised response to the task by replacing the one or more synthetic PHI parameters of the response with the one or more PHI parameters of the user request.

2. The method of embodiment 1, wherein the user request comprises text and the one or more trained machine learning models comprise a natural language processing (NLP) model, extracting the one or more PHI parameters associated with the patient comprises: inputting the text to the NLP model to identify the one or more PHI parameters associated with the patient from the user request.

3. The method of embodiment 2, wherein the NLP model is trained to populate a data structure representing the user request based on the text.

4. The method of embodiment 3, further comprising: parsing, using the NLP model, the text into a plurality of text tokens; determining, using the NLP model, a PHI parameter associated with each the plurality of text tokens; and populating, using the NLP model, the data structure with at least some of the plurality of text tokens associated with each of the one or more PHI parameters.

5. The method of embodiment 4, wherein the data structure comprises a plurality of data fields each corresponding to one of the one or more PHI parameters, wherein each data field stores a value comprising one or more of the plurality of text tokens associated with PHI parameter of the data field.

6. The method of any one of embodiments 1-5, wherein the user request comprises one or more images and the one or more trained machine learning models comprise a computer vision model, exacting the one or more PHI parameters associated with the patient comprises: inputting the one or more images to the computer vision model to determine the one or more PHI parameters associated with the patient from the user request.

7. The method of embodiment 6, wherein the computer vision model is trained to populate a data structure representing the user request based on the one or more images.

8. The method of embodiment 7, further comprising: detecting, using the computer vision model, one or more objects within at least one of the one or more images; determining, using the computer vision model and based on the one or more detected objects, a PHI parameter associated with each of the one or more objects; and populating, using the computer vision model, the data structure with at least some of the one or more detected objects associated with each of the one or more PHI parameters.

9. The method of embodiment 8, wherein the data structure comprises a plurality of data fields each corresponding to one of the one or more PHI parameters, and wherein each data field stores a value comprising an indication of at least one of the one or more objects associated with a PHI parameter of the data field.

10. The method of embodiment 5 or 9, further comprising: determining an intent of the user request based on the one or more PHI parameters, wherein the task is based on the intent.

11. The method of any one of embodiment 1-10, wherein the one or more PHI parameters comprise private information associated with the patient, and wherein at least some of the one or more synthetic PHI parameters comprise de-identified and anonymized versions of the private information associated with the patient.

12. The method of any one of embodiments 1-11, wherein the one or more PHI parameters comprise at least one of: a patient injury, a patient illness, a patient age, a body part associated with the patient injury, a body part associated with the patient illness, a patient location, a patient medical identification number, a patient name, a patient address, patient contact information, patient billing information, patient visit/test date, patient test results, patient image, patient medical image, or patient insurance information.

13. The method of any one of embodiments 1-12, further comprising: generating the one or more synthetic PHI parameters based on the one or more PHI parameters and clinical relevance data associated with the task.

14. The method of embodiment 13, wherein the clinical relevance data comprises a list of PHI parameters associated with the task and a relevancy score indicating how relevant each of the PHI parameters is to the task to be performed by the trained external machine learning model.

15. The method of embodiment 14, further comprising: determining the relevance score for each of the PHI parameters based on (i) a plurality of previous user requests comprising the task and (ii) a frequency that the PHI parameters were included in a plurality of previous responses to the plurality of previous user requests.

16. The method of embodiment 15, wherein the one or more trained machine learning models comprise an encoder, the method further comprises: inputting the user request to the encoder to obtain an encoded representation of the user request; computing a similarity score between the encoded representation and a plurality of encoded representations each associated with one of the plurality of previous user requests; and determining one or more of the plurality of previous user requests similar to the user request based on the ranking, wherein the clinical relevance data is selected from a clinical relevance database based on the clinical relevance data selected for the one or more of the plurality of previous user requests.

17. The method of embodiment 16, wherein the encoded representation comprises an embedding and the plurality of encoded representations comprises a plurality of embeddings, computing the similarity score comprises: computing a distance between the embedding and each of the plurality of embeddings.

18. The method of embodiment 17, wherein the one or more of the plurality of previous user requests are identified based on the distance between the embedding and an embedding of the plurality of embeddings corresponding to the one or more of the plurality of previous user requests being less than a threshold distance.

19. The method of embodiment 17 or embodiment 18, wherein the distance comprises an L2 distance, a Manhattan distance, or a Cosine distance.

20. The method of any one of embodiments 13-19, wherein generating the one or more synthetic PHI parameters comprises: receiving the clinical relevance data based on the task; and modifying at least some of the one or more PHI parameters based on the clinical relevance data to obtain the one or more synthetic PHI parameters.

21. The method of embodiment 20, wherein the clinical relevance data comprises a list of a plurality of PHI parameters associated with the task, a relevance score associated with each of the plurality of PHI parameters, and modification criteria associated with each of the plurality of PHI parameters, wherein the modification criteria indicates that the one or more PHI parameters of the plurality of PHI parameters associated with the task are to be selected for modification and how the one or more PHI parameters are to be modified.

22. The method of embodiment 21, wherein modifying comprises: for each of the one or more PHI parameters: identifying a randomness factor based on the modification criteria associated with the PHI parameter; and selecting, from a distribution of values of the PHI parameter, a value of the synthetic PHI parameter based on the randomness factor and a value of the PHI parameter from the user request.

23. The method of embodiment 22, wherein the randomness factor is inversely proportional to a relevance score associated with each of the one or more PHI parameters.

24. The method of any one of embodiments 1-23, further comprising: generating a mapping between the one or more PHI parameters of the user request and the one or more synthetic PHI parameters of the revised user request.

25. The method of embodiment 24, wherein generating the revised response comprises: accessing the mapping to determine which of the one or more PHI parameters are to replace each of the one or more synthetic PHI parameters.

26. The method of any one of embodiments 1-25, further comprising: training the one or more trained machine learning models using a corpus of electronic health records (EHRs) of a plurality of subjects.

27. The method of embodiment 26, wherein the one or more trained machine learning models comprise a plurality of specialized machine learning models each associated with a medical condition.

28. The method of embodiment 27, wherein the plurality of specialized machine learning models include at least one of: a cardiology-specific model trained on EHRs of subjects from the plurality of subjects diagnosed with one or more cardiological conditions; a pulmonary-specific model trained on EHRs of subjects from the plurality of subjects diagnosed with one or more pulmonary conditions; a pediatric-specific model trained on EHRs of subjects from the plurality of subjects having one or more pediatric conditions; a women's-health-specific model trained on EHRs of subjects from the plurality of subjects having one or more women's-health conditions; a sport-medicine-specific model trained on EHRs of subjects from the plurality of subjects having one or more sports-medicine conditions; or an oncology-specific model trained on EHRs of subjects from the plurality of subjects having one or more forms of cancers.

29. The method of embodiment 27 or 28, wherein each of the plurality of specialized machine learning models includes a model-specific set of PHI parameters associated with a corresponding medical condition.

30. The method of embodiment 29, further comprising: identifying the medical condition based on the user request; determining the task based on the medical condition; and selecting a specialized machine learning model from the plurality of specialized machine learning models based on the task, wherein the one or more PHI parameters are detected within the user request based on the model-specific set of PHI parameters associated with the selected specialized machine learning model.

31. The method of any one of embodiments 1-30, wherein the trained external machine learning model comprise a generative machine learning model.

32. The method of embodiment 31, wherein the generative machine learning model comprises a large language model (LLM).

33. The method of any one of embodiments 1-32, wherein the one or more trained machine learning models are deployed on a private computing environment and the trained external machine learning model is deployed on a public computing environment.

34. The method of any one of embodiments 1-33, wherein a structure of the response is determined based on the task.

35. The method of any one of embodiments 1-34, wherein the user request is input via an application programming interface (API) prompt.

36. The method of any one of embodiments 1-35, further comprising: determining whether the user request is part of an existing session between a client device and the trained external machine learning model.

37. The method of embodiment 36, further comprising: appending a history of the existing session to include the user request based on the user request being determined to be part of the existing session.

38. The method of embodiment 36, further comprising: creating a new session between the client device and the trained external machine learning model, wherein the new session includes the user request; and adding the response to the task and the revised response to the task to a history of the new session.

39. The method of any one of embodiments 1-38, further comprising: obtaining patient health data associated with a plurality of patients; extracting, using the one or more trained machine learning models, a set of PHI parameters associated with each of the plurality of patients; generating, using the one or more trained machine learning models, anonymized patient health data by replacing, for each patient, the set of PHI parameters with a corresponding set of synthetic PHI parameters.

40. The method of embodiment 39, further comprising: training a non-anonymized machine learning model using the anonymized patient health data, wherein the trained non-anonymized machine learning model is not trained using the set of PHI parameters associated with the plurality of patients.

41. A method for training a non-anonymized machine learning model, the method comprising: obtaining patient health data associated with a plurality of patients; extracting, using one or more trained machine learning models, one or more protected health information (PHI) parameters from the patient health data associated with the plurality of patients; generating, using the one or more trained machine learning models, anonymized patient health data by replacing the one or more PHI parameters extracted from the patient health data with one or more synthetic PHI parameters; and training a non-anonymized machine learning model using the anonymized patient health data to obtain a trained anonymized machine learning model, wherein trained anonymized machine learning model protects the patient health data associated with the plurality of patients from data leaks.

42. A system comprising: one or more processors programmed to perform the method of any one of embodiments 1-41.

43. A non-transitory computer-readable medium storing computer program instructions that, when executed by one or more processors of a computing system, effectuate operations comprising the method of any one of embodiments 1-41.

What We claim is:

1. A method for performing a task using a trained external machine learning model, comprising:
   receiving a user request comprising the task and one or more protected health information (PHI) parameters associated with a patient;
   extracting, using one or more trained machine learning models, the one or more PHI parameters associated with the patient;
   generating, using the one or more trained machine learning models, one or more synthetic PHI parameters based on the one or more PHI parameters and clinical relevance data associated with the task, wherein generating the one or more synthetic PHI parameters comprises receiving the clinical relevance data based on the task and modifying at least some of the one or more PHI parameters based on the clinical relevance data to obtain the one or more synthetic PHI parameters;
   generating, using the one or more trained machine learning models, a revised user request by replacing the one or more PHI parameters in the user request with the one or more synthetic PHI parameters;
   providing the revised user request to the trained external machine learning model;
   receiving, from the trained external machine learning model, a response to the task comprising the one or more synthetic PHI parameters; and
   generating, using the one or more trained machine learning models, a revised response to the task by replacing the one or more synthetic PHI parameters of the response with the one or more PHI parameters of the user request.

2. The method of claim 1, wherein the user request comprises text and the one or more trained machine learning models comprise a natural language processing (NLP) model, extracting the one or more PHI parameters associated with the patient comprises:
   inputting the text to the NLP model to identify the one or more PHI parameters associated with the patient from the user request.

3. The method of claim 2, wherein the NLP model is trained to populate a data structure representing the user request based on the text, the method further comprising:
   parsing, using the NLP model, the text into a plurality of text tokens;
   determining, using the NLP model, a PHI parameter associated with each the plurality of text tokens; and
   populating, using the NLP model, the data structure with at least some of the plurality of text tokens associated with each of the one or more PHI parameters.

4. The method of claim 1, wherein the user request comprises one or more images and the one or more trained machine learning models comprise a computer vision model, extracting the one or more PHI parameters associated with the patient comprises:

inputting the one or more images to the computer vision model to determine the one or more PHI parameters associated with the patient from the user request.

5. The method of claim 4, wherein the computer vision model is trained to populate a data structure representing the user request based on the one or more images, the method further comprising:

detecting, using the computer vision model, one or more objects within at least one of the one or more images;

determining, using the computer vision model and based on the one or more detected objects, a PHI parameter associated with each of the one or more objects; and populating, using the computer vision model, the data structure with at least some of the one or more detected objects associated with each of the one or more PHI parameters.

6. The method of claim 1, wherein the one or more PHI parameters comprise private information associated with the patient, and wherein at least some of the one or more synthetic PHI parameters comprise de-identified and anonymized versions of the private information associated with the patient.

7. The method of claim 1, wherein the clinical relevance data comprises a list of PHI parameters associated with the task and a relevancy score indicating how relevant each of the PHI parameters is to the task to be performed by the trained external machine learning model, the method further comprising: determining the relevance score for each of the PHI parameters based on (i) a plurality of previous user requests comprising the task and (ii) a frequency that the PHI parameters were included in a plurality of previous responses to the plurality of previous user requests.

8. The method of claim 1, wherein the clinical relevance data comprises a list of a plurality of PHI parameters associated with the task, a relevance score associated with each of the plurality of PHI parameters, and modification criteria associated with each of the plurality of PHI parameters, wherein the modification criteria indicates that the one or more PHI parameters of the plurality of PHI parameters associated with the task are to be selected for modification and how the one or more PHI parameters are to be modified.

9. The method of claim 1, further comprising:

generating a mapping between the one or more PHI parameters of the user request and the one or more synthetic PHI parameters of the revised user request, wherein generating the revised response comprises accessing the mapping to determine which of the one or more PHI parameters are to replace each of the one or more synthetic PHI parameters.

10. The method of claim 1, wherein the one or more trained machine learning models comprise a plurality of specialized machine learning models each associated with a medical condition, wherein each of the plurality of specialized machine learning models includes a model-specific set of PHI parameters associated with a corresponding medical condition.

11. The method of claim 10, further comprising:

identifying the medical condition based on the user request;

determining the task based on the medical condition; and selecting a specialized machine learning model from the plurality of specialized machine learning models based on the task, wherein the one or more PHI parameters are detected within the user request based on the model-specific set of PHI parameters associated with the selected specialized machine learning model.

12. The method of claim 1, wherein the trained external machine learning model comprises a large language model (LLM).

13. The method of claim 1, wherein the one or more trained machine learning models are deployed on a private computing environment and the trained external machine learning model is deployed on a public computing environment.

14. The method of claim 1, further comprising:

determining whether the user request is part of an existing session between a client device and the trained external machine learning model;

appending a history of the existing session to include the user request based on the user request being determined to be part of the existing session;

creating a new session between the client device and the trained external machine learning model, wherein the new session includes the user request; and adding the response to the task and the revised response to the task to a history of the new session.

15. The method of claim 1, further comprising:

obtaining patient health data associated with a plurality of patients;

extracting, using the one or more trained machine learning models, a set of PHI parameters associated with each of the plurality of patients;

generating, using the one or more trained machine learning models, anonymized patient health data by replacing, for each patient, the set of PHI parameters with a corresponding set of synthetic PHI parameters; and training a non-anonymized machine learning model using the anonymized patient health data, wherein the trained non-anonymized machine learning model is not trained using the set of PHI parameters associated with the plurality of patients.

16. A system for performing a task using a trained external machine learning model, comprising:

one or more processors, a memory, and one or more programs, wherein the one or more programs are stored in the memory and configured to be executed by the one or more processors, the one or more programs including instructions for:

receiving a user request comprising the task and one or more protected health information (PHI) parameters associated with a patient;

extracting, using one or more trained machine learning models, the one or more PHI parameters associated with the patient;

generating, using the one or more trained machine learning models, one or more synthetic PHI parameters based on the one or more PHI parameters and clinical relevance data associated with the task, wherein generating the one or more synthetic PHI parameters comprises receiving the clinical relevance data based on the task and modifying at least some of the one or more PHI parameters based on the clinical relevance data to obtain the one or more synthetic PHI parameters;

generating, using the one or more trained machine learning models, a revised user request by replacing the one or more PHI parameters in the user request with the one or more synthetic PHI parameters;

providing the revised user request to the trained external machine learning model;

receiving, from the trained external machine learning model, a response to the task comprising the one or more synthetic PHI parameters; and generating, using the one or more trained machine learning models, a revised response to the task by replacing the one or more synthetic PHI parameters of the response with the one or more PHI parameters of the user request.

17. A non-transitory computer-readable medium storing computer program instructions performing a task using a trained external machine learning model that, when executed by one or more processors of a computing system, effectuate operations comprising receive a user request comprising the task and one or more protected health information (PHI) parameters associated with a patient;

extract, using one or more trained machine learning models, the one or more PHI parameters associated with the patient;

generate, using the one or more trained machine learning models, one or more synthetic PHI parameters based on the one or more PHI parameters and clinical relevance data associated with the task, wherein generating the one or more synthetic PHI parameters comprises receiving the clinical relevance data based on the task and modifying at least some of the one or more PHI parameters based on the clinical relevance data to obtain the one or more synthetic PHI parameters;

generate, using the one or more trained machine learning models, a revised user request by replacing the one or more PHI parameters in the user request with the one or more synthetic PHI parameters;

provide the revised user request to the trained external machine learning model;

receive, from the trained external machine learning model, a response to the task comprising the one or more synthetic PHI parameters; and generate, using the one or more trained machine learning models, a revised response to the task by replacing the one or more synthetic PHI parameters of the response with the one or more PHI parameters of the user request.

* * * * *